US006805876B2

(12) United States Patent
Leong et al.

(10) Patent No.: US 6,805,876 B2
(45) Date of Patent: Oct. 19, 2004

(54) PHOSPHATE BASED BIODEGRADABLE POLYMERS

(75) Inventors: Kam W. Leong, Ellicott City, MD (US); Wen Jie, Baltimore, MD (US); Ren-Xi Zhuo, Wuhan (CN); Hai-Quan Mao, Singapore (SG)

(73) Assignee: Johns Hopkins University, Baltimore, MD (US)

( * ) Notice: Subject to any disclaimer, the term of this patent is extended or adjusted under 35 U.S.C. 154(b) by 41 days.

(21) Appl. No.: 09/803,358

(22) Filed: Mar. 10, 2001

(65) Prior Publication Data

US 2002/0155092 A1 Oct. 24, 2002

Related U.S. Application Data

(60) Provisional application No. 60/188,477, filed on Mar. 10, 2000.

(51) Int. Cl.[7] ............................ A61F 2/02; A61K 47/30; C08G 79/02
(52) U.S. Cl. ..................... 424/426; 514/772.3; 523/111; 523/113; 528/398
(58) Field of Search ...................... 424/426; 514/772.3; 528/398; 523/111, 113

(56) References Cited

U.S. PATENT DOCUMENTS 6,166,173 A * 12/2000 Mao et al. .................. 528/398

FOREIGN PATENT DOCUMENTS

| EP | 0 386 757 A2 | 3/1990 |
| WO | WO 98/44020 | 4/1998 |
| WO | WO 98/48859 | 4/1998 |
| WO | WO 98/46286 | 10/1998 |

OTHER PUBLICATIONS

Copy of EPO International Search Report, (18) pages, Mail date Nov. 8, 1998.

* cited by examiner

Primary Examiner—Carlos A. Azpuru
(74) Attorney, Agent, or Firm—Peter F. Corless; John B. Alexander; Edwards & Angell, LLP

(57) ABSTRACT

Featured are biodegradable polymers comprising repeat units derived from cyclic phosphate monomers and optionally further comprising repeat units derived from lactide or caprolactone monomers. Also featured are methods for preparing the biodegradable polymers of the invention and biodegradable polymer compositions comprising a biologically active substance and a biodegradable polymer. Additionally featured are articles and microspheres prepared from biodegradable polymers and polymer compositions of the invention. Further, methods for the controlled release of a biologically active substance using the biodegradable polymers of the invention are also described.

27 Claims, 9 Drawing Sheets

PHOSPHATE BASED BIODEGRADABLE POLYMERS

This application claims the benefit of U.S. Provisional Application Serial No. 60/188,477 filed Mar. 10, 2000, the teachings of which are incorporated herein by reference.

BACKGROUND OF THE INVENTION

1. Field of the Invention

The present invention relates to biodegradable and biocompatible polymer compositions and more particularly to biodegradable copolymers and terpolymers; methods used for preparation of the recited polymers; articles useful for implantation or injection into the human body that are fabricated from said compositions; and, methods for the controlled release of biologically active substances.

2. Background

Biocompatible polymeric materials have been used extensively in therapeutic drug delivery and medical implant device applications. Sometimes, it is also desirable for such polymers to be, not only biocompatible, but also biodegradable to obviate the need for removing the polymer once its therapeutic value has been exhausted.

Conventional methods of drug delivery, such as frequent periodic dosing, are not ideal in many cases. For example, with highly toxic drugs, frequent conventional dosing can result in high initial drug levels at the time of dosing, often at near-toxic levels, followed by low drug levels between doses that can be below the level of their therapeutic value. However, with controlled drug delivery, drug levels can be more nearly maintained at therapeutic, but non-toxic, levels by controlled release in a predictable manner over a longer term.

If a biodegradable medical device is intended for use as a drug delivery or other controlled-release system, using a polymeric carrier is one effective means to deliver the therapeutic agent locally and in a controlled fashion, see Langer et al., Rev. Macro. Chem. Phys., C23(1), 61 (1983). As a result, less total drug is required, and toxic side effects can be minimized. Polymers have been used as carriers of therapeutic agents to effect a localized and sustained release. See Chien et al., Novel Drug Delivery Systems (1982). Such delivery systems offer the potential of enhanced therapeutic efficacy and reduced overall toxicity.

For a non-biodegradable matrix, the steps leading to release of the therapeutic agent are water diffusion into the matrix, dissolution of the therapeutic agent, and diffusion of the therapeutic agent out through the channels of the matrix. As a consequence, the mean residence time of the therapeutic agent existing in the soluble state is longer for a non-biodegradable matrix than for a biodegradable matrix, for which passage through the channels of the matrix, while it may occur, is no longer required. Since many pharmaceuticals have short half-lives, therapeutic agents can decompose or become inactivated within the non-biodegradable matrix before they are released. This issue is particularly significant for many bio-macromolecules and smaller polypeptides, since these molecules are generally hydrolytically unstable and have low permeability through a polymer matrix. In fact, in a non-biodegradable matrix, many bio-macromolecules aggregate and precipitate, blocking the channels necessary for diffusion out of the carrier matrix.

These problems are alleviated by using a biodegradable matrix that, in addition to some diffusional release, also allows controlled release of the therapeutic agent by degradation of the polymer matrix. Examples of classes of synthetic polymers that have been studied as possible biodegradable materials include polyesters (Pitt et al., Controlled Release of Bioactive Materials, (Baker, ed. 1980); polyamides; polyurethanes; polyorthoesters (Heller et al., Polymer Engineering Sci., 21:727 (1981); and polyanhydrides (Leong et al., Biomaterials 7:364 (1986). Specific examples of biodegradable materials that are used as medical implant materials are polylactide, polyglycolide, polydioxanone, poly(lactide-co-glycolide), poly(glycolide-co-polydioxanone), polyanhydrides, poly(glycolide-co-trimethylene carbonate), and poly(glycolide-co-caprolactone).

Polymers having phosphate linkages, called poly (phosphates), poly(phosphonates) and poly(phosphites), are known. The respective structures of these three classes of compounds, each having a different sidechain connected to the phosphorus atom, are as follows:

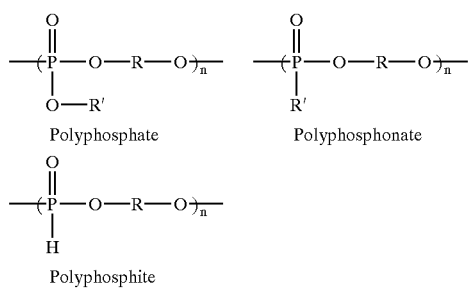

The versatility of these polymers comes from the versatility of the phosphorus atom, which is known for a multiplicity of reactions. Its bonding can involve the 3p orbitals or various 3s–3p hybrids; spd hybrids are also possible because of the accessible d orbitals. Thus, the physicochemical properties of the poly(phosphoesters) can be readily changed by varying either the R or R' group. The biodegradability of the polymer is due primarily to the physiologically labile phosphoester bond in the backbone of the polymer. By manipulating the backbone or the sidechain, a wide range of biodegradation rates are attainable.

An additional feature of poly(phosphoesters) is the availability of functional side groups. Because phosphorus can be pentavalent, drug molecules or other biologically active substances can be chemically linked to the polymer, as shown by Leong, U.S. Pat. Nos. 5,194,581 and 5,256,765. For example, drugs with —O-carboxy groups may be coupled to the phosphorus via an ester bond, which is hydrolyzable. The P—O—C group in the backbone also lowers the glass transition temperature of the polymer and, importantly, confers solubility in common organic solvents, which is desirable for easy characterization and processing.

Polylactide, referred to herein as PLA, and poly(lactide-co-glycolide), referred to herein as PLGA, are among the most popular and well characterized biodegradable polymeric materials used today for drug delivery and tissue engineering. Further, the present invention provides the ability to incorporate side chain modifications into both PLA and PLGA.

The growing needs in biomedical practice have continued to stimulate the studies for developing new biodegradable materials. Although several classes of synthetic polymers, including polyesters, poly(amino acid)s/polyamides, polyurethanes, poly(orthoester)s, poly(anhydride)s, polycarbonates, poly(imidocarbonate)s, and poly (phosphazene)s, have been studied for controlled drug delivery and tissue engineering, polylactide (PLA) and poly (lactide-co-glycolide) (PLGA) still remain the most popular and well characterized bio degradable polymeric biomaterials. Their regulatory approval and extensive database of human use render them obvious choice in contemplating a medical application that ranges from controlled drug delivery to tissue engineering.

The widening scope of applications in controlled delivery and tissue engineering require the biomaterials to assume different configurations to serve different functions. Applying the controlled release device as more than just a monolithic matrix, for example, as coating materials for a drug-eluting stent, may obligate the polymer to have elastomeric properties. In the new and exciting field of tissue engineering where local and sustained delivery of growth factors may influence the course of tissue development, the polymeric drug-carriers may also need to provide structural support or scaffolding functions. With such a broad utility for these biodegradable materials, PLA and PLGA cannot be expected to satisfy all requirements of different applications.

Besides physical blending, one of the most plausible ways to adjust the physico-chemical properties of PLA and PLGA is through copolymerization. Lactide copolymers with different constituent monomers can offer a broad range of physico-chemical properties and degradation rates. Poly (lactide-co-ester)s [e.g. (lactide-co-caprolactone)], poly (lactide-co-ether)s [e.g. poly(dioxanone), poly(ethylene glycol-b-lactide)], poly(lactide-co-carbonate) [e.g. poly (lactide-co-1,3-dioxan-2-one)], and poly(lactide-co-amide)s [poly(lactide-co-L-lysine)] are a few of the examples that have been evaluated so far.

Mao et al. (Mao, H.-Q., Z. Zhao, J. P. English and K. W. Leong (1997), Biodegradable polymers chain-extended byphosphoesters, compositions, articles and methods for making and using the same. U.S. Pat. No. 6,166,173) synthesized oligomeric lactide chain extended with alkyl phosphate in step growth polymerization processes. The resulting polymers had a more linear in vitro and in vivo degradation, compared with PLA with a similar molecular weight. However, compositions could only be prepared with a narrow range of phosphate incorporation, limiting the extent to which physical properties of the composition could be modified. The overall physico-chemical properties were similar to PLA/PLGA.

Fan et al. (Fan, C.-L., B. Li, Z.-H. Liu, R.-X. Zhuo (1995), A study on ring-opening copolymerization of D,L-lactide and 2-hydro-2-oxo-1,3,2-dioxaphosphorinane, Chemical Journal of Chinese Universities, 16(6), 971–973) have studied the random polymerization of D,L-lactide and 2-hydro-2-oxo-1,3,2-dioxaphosphorinane in the presence of triisobutylaluminum. The resulting copolymers are crosslinked, resulting in poor polymer solubility in both organic and aqueous solvents. 5-Fluorouracil (5-FU) was conjugated to the side chain of phosphite group. The release of 5-FU was close to first order release (Fan, C.-L., B. Li, Z.-H. Liu, R.-X. Zhuo (1996), Studies on synthesis and controlled release of polymeric drug using lactide-phosphate copolymer as drug carriers, Chemical Journal of Chinese Universities, 17(11), 1788–1791). The poor solubility of these polymers make them unsuitable for use in the present invention.

SUMMARY OF THE INVENTION

The present invention is directed to a series of biodegradable, biocompatible polymers comprising repeat units derived from cyclic phosphate monomers, e.g., ethylene methyl phosphate and the like, and optionally comprising repeat units derived from functionalized lactones and functionalized glycolide derivatives, e.g., (L,L)-lactide, (D,D)-lactide, meso-lactide, mixtures thereof and the like. The polymers of the invention have unique structures and physico-chemical properties.

Polymers of the invention comprise phosphoester backbone linkages which offers several advantages including (1) adjustable properties because the structures of both the backbone and the side chain can be varied; (2) lower glass transition temperature end better solvent solubility because of the plasticizing effect of the phosphate bond; (3) a natural candidate for a biodegradable pendant delivery system because of the availability of a functional side chain; (4) potentially nontoxic breakdown products because of a backbone analogous to nucleic acid and teichoic acid. Copolymerization between lactide and phosphate brings hydrophilicity, flexibility, and the ability of side chain modification to PLA and PLGA systems.

The present invention features biodegradable polymers, the polymers comprise at least one repeat unit according to formula A:

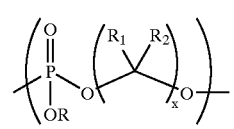

wherein

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;

$R^1$ and $R^2$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

x is 2, 3, or 4; and at least one repeat unit selected from the group consisting of optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl, —O(CR$_1$R$_2$)$_c$C(O)— where c is between about 1 and about 10, —(CH$_2$)$_a$—{O(CH$_2$)$_a$}$_b$— where a is between about 1 and about 7 and b is between about 1 and about 500, optionally substituted aryl, and optionally substituted heteroaryl; or at least one repeat unit according to formula B:

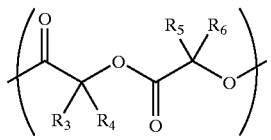

wherein
$R^3$, $R^4$, $R^5$ and $R^6$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy.

The biodegradable polymers of the present invention are biocompatible before and upon biodegradation.

Preferred polymers of the invention can be either linear or branched and are preferably substantially free of interpolymer chain crosslinking.

Preferred polymers of the invention comprise either lactide derived repeat units according to formula B:

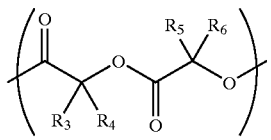

wherein
$R^3$, $R^4$, $R^5$ and $R^6$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl, and optionally substituted alkoxy preferably optionally substituted $C_{1-12}$-alkoxy;
or caprolactone derived repeat units, e.g., —O(CR$_1$R$_2$)$_c$C(O)— where c is between about 1 and about 10, preferably c is between about 3 and about 6 more preferably c is about 5.

The biodegradable polymers of the invention exhibit unique physiochemical properties when compared to PLA and PLGA.

The present invention also features a process for preparing a biodegradable polymer comprising the recurring monomeric units of formula I:

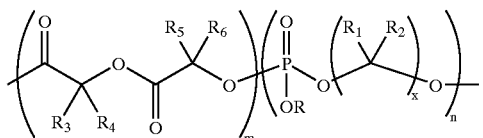

wherein:
R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;

$R^1$ and $R^2$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted $C_{1-12}$-alkoxy;

x is 2, 3, or 4;

n and m are non-negative integers;

n+m is about 5 to about 2000; and m:n is between about 1:100 to about 100:1;

wherein the biodegradable polymer is biocompatible before and upon biodegradation processes occur, the process comprising the steps of:

contacting a glycolide derivative and a cyclic phosphate under conditions conducive to the formation of a biodegradable polymer comprising repeat units originating from the glycolide derivative and the cyclic phosphate.

The present invention also features a process for preparing a biodegradable polymer comprising the recurring monomeric units of formula III:

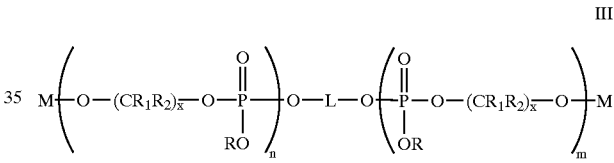

wherein:
R is hydrogen, optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted alkyl preferably optionally substituted $C_{1-12}$-alkyl;

$R^1$ and $R^2$ are each independently chosen at each occurrence from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

L is chosen from the group consisting of optionally substituted alkyl preferably optionally substituted $C_{2-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl or —(CH$_2$)$_a$—{O—(CH$_2$)$_a$}$_b$—, wherein each a is 1–6 and b is 1–500;

n and m are non-negative integers;

n+m is about 5 to about 2000;

x is 2, 3 or 4; and

M is independently chosen at each occurrence of M from the group consisting of H, Na, Li, and K;

the process comprising the steps of:

contacting at least one cyclic phosphate with an initiator compound, HO—L—OH;

polymerizing the cyclic phosphate with the initiator compound under conditions conducive to preparing the biodegradable polymer.

The present invention also features a process for preparing a biodegradable polymer comprising the recurring monomeric repeat units of formula V:

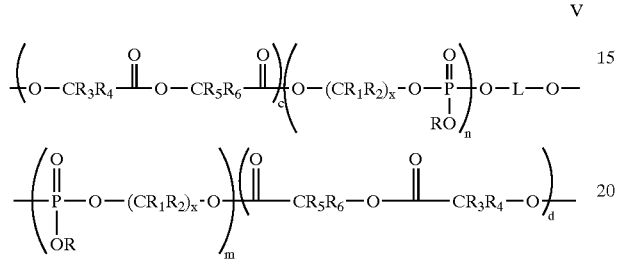

wherein

L is optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-20}$-heteroalkyl, —$(CH_2)_a$—$\{O(CH_2)_a\}_b$ where a is between about 1 and about 7 and b is between about 1 and about 500, optionally substituted aryl, or optionally substituted heteroaryl;

x is 2, 3, or 4;

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-20}$-heteroalkyl, or optionally substituted cycloalkyl preferably optionally substituted $C_{5-8}$-cycloalkyl;

$R^1$ and $R^2$ are each independently chosen from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl, and optionally substituted alkoxy preferably optionally substituted $C_{1-12}$-alkoxy;

n and m are non-negative integers;

n+m is about 5 to about 2000;

m:n is between about 1:100 to about 100:1;

c and d are non-negative integers;

c+d is about 5 to about 2000;

(m+n):(c+d) is between about 1:100 and 100:1; and, the process comprising the steps of:

making at least one biodegradable polymer of claim 13;

contacting the biodegradable polymer of claim 13 with at least one glycolide derivative; and polymerizing the glycolide derivative under conditions conducive to the preparing a biodegradable polymer according to formula V.

The present invention also features biodegradable polymer composition comprising:

(a) at least one biologically active substance; and (b) a biodegradable polymer comprising at least one repeat unit according to formula A:

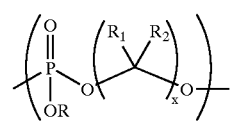

wherein

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;

$R^1$ and $R^2$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

x is 2, 3, or 4; and at least one repeat unit selected from the group consisting of optionally substituted alkyl preferably optionally substituted $C_{1-12}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl, —$O(CR_1R_2)_cC(O)$— where c is between about 1 and about 10, —$(CH_2)_a$—$\{O(CH_2)_a\}_b$— where a is between about 1 and about 7 and b is between about 1 and about 500, optionally substituted aryl, and optionally substituted heteroaryl; or at least one repeat unit according to formula B:

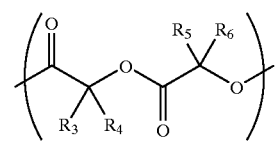

wherein $R^3$, $R^4$, $R^5$ and $R^6$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy.

The present invention also features an article useful for implantation, injection, or otherwise being placed totally or partially within a body, the article comprising a biodegradable polymer composition comprising:

(a) at least one biologically active substance; and
(b) a biodegradable polymer comprising at least one repeat unit according to formula A:

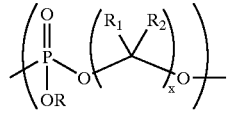

wherein
R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;

$R^1$ and $R^2$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

x is 2, 3, or 4; and at least one repeat unit selected from the group consisting of optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl, $-O(CR_1R_2)_cC(O)-$ where c is between about 1 and about 10, $-(CH_2)_a-\{O(CH_2)_a\}_b-$ where a is between about 1 and about 7 and b is between about 1 and about 500, optionally substituted aryl, and optionally substituted heteroaryl; or at least one repeat unit according to formula B:

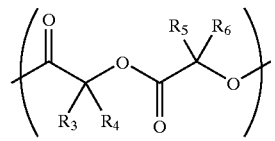

wherein
$R^3$, $R^4$, $R^5$ and $R^6$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy.

In preferred embodiments the biodegradable polymer is biocompatible before and upon biodegradation The present invention also features a method for the controlled release of at least one biologically active substance comprising the steps of:

(a) combining the biologically active substance with a biodegradable polymer comprising at least one repeat unit according to formula A:

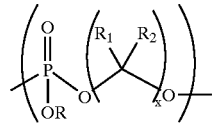

wherein
R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;

$R^1$ and $R^2$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

x is 2, 3, or 4; and at least one repeat unit selected from the group consisting of optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl, $-O(CR_1R_2)_cC(O)-$ where c is between about 1 and about 10, $-(CH_2)_a-\{O(CH_2)_a\}_b-$ where a is between about 1 and about 7 and b is between about 1 and about 500, optionally substituted aryl, and optionally substituted heteroaryl; or at least one repeat unit according to formula B:

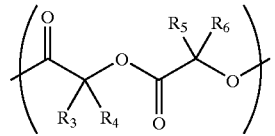

wherein
$R^3$, $R^4$, $R^5$ and $R^6$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

to form an admixture;

(b) forming said admixture into a shaped, solid article or microsphere; and (c) implanting or injecting the solid article or microsphere in vivo at a preselected site, such that the solid implanted or injected matrix is in at least partial contact with a biological fluid.

U.S. Pat. Nos. 5,912,225 entitled "Biodegradable Poly (phosphoester-Co-Desaminotyrosyl L-Tyrosine Ester) Compounds, Compositions, Articles and Methods for Making and Using the Same" and U.S. Pat. No. 6,166,173 entitled "Biodegradable Polymers Chain Extended by Phosphates, Compositions, Articles and Methods for Making and Using the Same" are incorporated herein by reference in their entirety.

BRIEF DESCRIPTION OF THE DRAWING

For a fuller understanding of the present invention, reference is made to the following detailed description taken in conjunction with the accompanying figures wherein.

DETAILED DESCRIPTION OF THE INVENTION

Figure 1:
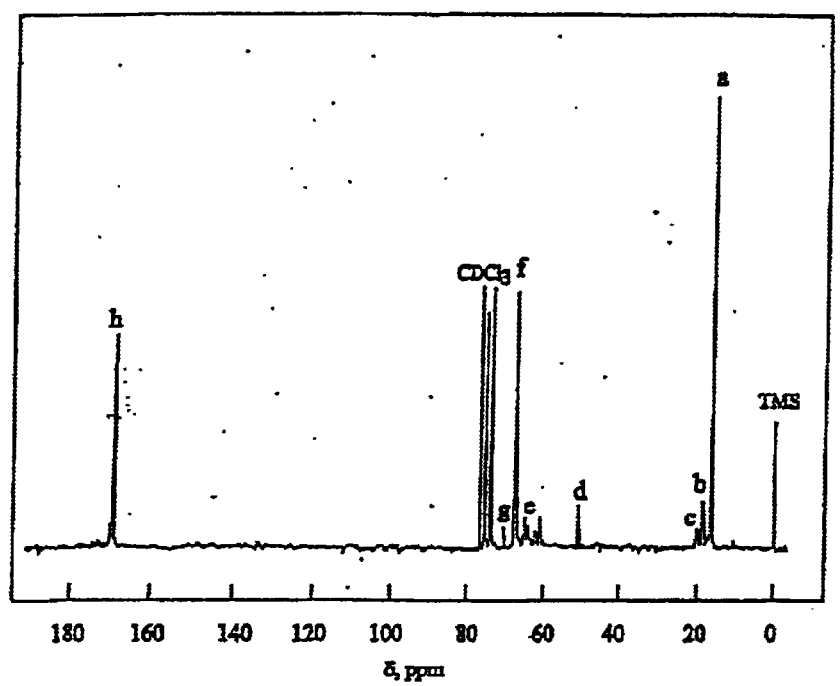
FIG. 1 is a $^{13}$C-NMR spectrum of poly(D,L-lactide-co-ethylene methyl phosphate)

The present invention features biodegradable polymer comprising at least one phosphate monomer repeat unit and at least one second monomer repeat unit, the second monomer repeat unit selected from the group consisting of optionally substituted glycyl glycolate, optionally substituted alkyl, optionally substituted alkenyl, optionally substituted alkynyl, optionally substituted heteroalkyl, optionally substituted heteroalkenyl, optionally substituted heteroalkynyl, optionally substituted alkyl hydroxy-ester and optionally substituted poly(ethylene glycol).

A preferred biodegradable polymer of the invention comprises repeat units as in formula I:

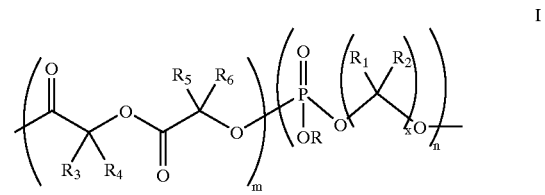

wherein

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;

$R^1$ and $R^2$ are each independently chosen from the group consisting of H, optionally substituted alkyl preferably optionally substituted $C_{2-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted $C_{1-12}$-alkoxy;

x is 2, 3, or 4;

n and m are non-negative integers;

n+m is about 5 to about 2000; and m:n is between about 1:100 to about 100:1.

The biodegradable polymer according to formula I are biodegradable and biocompatible before and upon biodegredation.

Additional preferred biodegradable polymers according to formula I include polymers wherein:

x is 2;

R is $C_{1-6}$-alkyl;

$R^1$ and $R^2$ are independently selected at each occurrence from the group consisting of hydrogen, methyl and ethyl;

$R^3$ and $R^5$ are hydrogen;

$R^4$ is hydrogen or $C_{1-6}$-alkyl; and, $R^6$ is $C_{1-6}$-alkyl.

Additional preferred biodegradable polymers according to formula I include polymers wherein:

x is 2;

R is methyl or ethyl;

$R^4$ and $R^6$ are methyl; and, $R^1$, $R^2$, $R^3$ and $R^5$ are hydrogen.

Additional preferred biodegradable polymers according to formula I include polymers wherein:

x is 2;

R is independently selected for each occurrence of R from the group consisting of hydrogen and $C_{1-6}$-alkyl, wherein at least some occurrence of R is hydrogen;

$R^1$ and $R^2$ are independently selected at each occurrence from the group consisting of hydrogen, methyl and ethyl;

$R^3$ and $R^5$ are hydrogen;

$R^4$ is hydrogen or $C_{1-6}$-alkyl; and, $R^6$ is $C_{1-6}$-alkyl.

Additional preferred biodegradable polymers according to formula I include polymers wherein:

x is 2;

R is independently selected for each occurrence of R from the group consisting of hydrogen and $C_{1-6}$-alkyl, wherein at least some occurrence of R is hydrogen;

$R^4$ and $R^6$ are methyl; and, $R^1$, $R^2$, $R^3$ and $R^5$ are hydrogen.

Preferred biodegradable polymers according to formula I include polymers according to formula II:

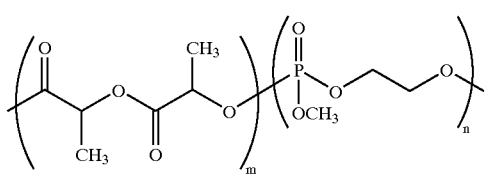

wherein n and m are non-negative integers;

n+m is about 5 to about 2000; and m:n is between about 1:100 to about 100:1.

The biodegradable polymer according to formula II are biodegradable and biocompatible before and upon biodegradation.

Preferred biodegradable polymers according to formula I include polymers according to formula IIA:

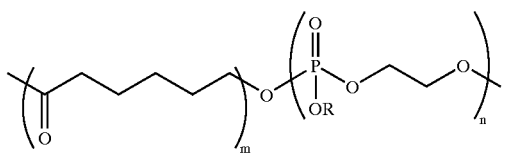

wherein

R is methyl or ethyl;

n and m are non-negative integers;

n+m is about 5 to about 2000; and m:n is between about 1:100 to about 100:1.

The biodegradable polymer according to formula IIA are biodegradable and biocompatible before and upon biodegradation.

Biodegradable polymers of the invention according to any of formula I, II or IIA include polymers wherein each of m and n is about 10 to 1,000. Preferably each of m and n is about 10 to 500. Moreover, preferred polymers of the invention according to formula I or II include polymers wherein the molar ratio, m:n, is between about 1:100 to about 100:1, more preferably between about 1:50 to about 50:1 and particularly preferably between about 1:20 and 20:1.

Biodegradable polymers of the invention according to any of formula I or II include polymers prepared by a melt polymerization or a Lewis acid catalyzed polymerization. Preferred melt polymerizations typically occur between about 70° C. and about 235° C., preferably between about 100° C. and 200° C., more preferably between 140° C. and 170° C. Preferred Lewis acid catalysts for Lewis acid catalyzed polymerizations include aluminum complexes such as trialkoxy aluminum, trialkyl aluminum and the like, zinc complexes such as dialkoxy zinc, diaryloxy zinc, diamido zinc, dialkyl zinc and the like, dicarboxylate tin(II) such as tin(II)bis(2-octanoate) and the like, and organometallic and metal-alkoxide complexes of other metals such as calcium, magnesium, cadmium, mercury, gallium, boron, copper, nickel and the like.

Preferred biodegradable polymers of the invention comprise repeat units as in formula III:

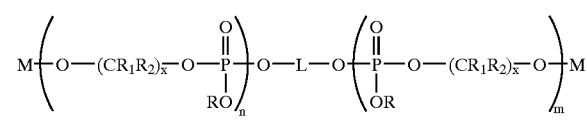

wherein

R is hydrogen, optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted alkyl preferably optionally substituted $C_{1-12}$-alkyl;

$R^1$ and $R^2$ are each independently chosen at each occurrence from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

L is chosen from the group consisting of optionally substituted alkyl preferably optionally substituted $C_{2-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl or —$(CH_2)_a$—$\{O(CH_2)_a\}_b$—, wherein each a is 1–6 and b is 1–500;

n and m are non-negative integers;

n+m is about 5 to about 2000;

x is 2, 3 or 4; and

M is independently chosen at each occurrence from the group consisting of H, Na, Li, and K.

The biodegradable polymers according to formula III are biodegradable and biocompatible before and upon biodegradation.

Additional preferred biodegradable polymers according to formula III include polymers wherein:

x is 2;

M is hydrogen;

R is $C_{1-6}$-alkyl; and, $R^1$ and $R^2$ are independently selected at each occurrence from the group consisting of hydrogen, methyl and ethyl.

Additional preferred biodegradable polymers according to formula III include polymers wherein:

L is —(CH$_2$)$_a$—{O(CH$_2$)$_a$}$_b$ where a is between about 1 and about 7 and b is between about 1 and about 500;

x is 2;

R is methyl or ethyl; and,

R$^1$ and R$^2$ are hydrogen.

Biodegradable polymers of the invention according to formula III include polymers wherein each of m and n is about 10 to 1,000. Preferably each of m and n is about 10 to 500. Moreover, preferred polymers of the invention according to formula III include polymers wherein the molar ratio, m:n, is between about 1:50 to about 50:1, more preferably between about 1:20 to about 20:1 and particularly preferably between about 1:5 and 5:1.

Biodegradable polymers of the invention according to formula III include polymers prepared by an anionic polymerization method. Preferred polymerizations typically occur between about 0° C. and about 235° C., preferably between about 20° C. and 150° C., more preferably between 40° C. and 90° C. Preferred initiators, MO—L—OM, include metal alkoxides such as where M is Li, Na, K and the like.

A preferred biodegradable polymer of the invention comprises repeat units as in formula IV:

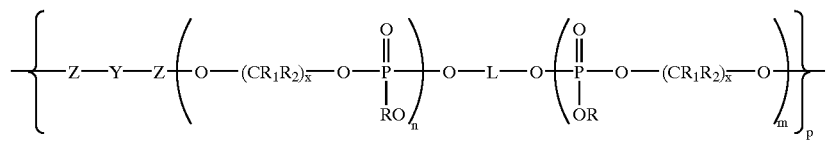

wherein
L is optionally substituted alkyl preferably optionally substituted C$_{1-20}$-alkyl, optionally substituted alkenyl preferably optionally substituted C$_{2-12}$-alkenyl, optionally substituted alkynyl preferably optionally substituted C$_{2-12}$-alkynyl, optionally substituted heteroalkyl preferably optionally substituted C$_{2-12}$-heteroalkyl, —(CH$_2$)$_a$—{O(CH$_2$)$_a$}$_b$ where a is between about 1 and about 7 and b is between about 1 and about 500, optionally substituted aryl, or optionally substituted heteroaryl;

x is 2, 3, or 4;

R is hydrogen, optionally substituted alkyl preferably optionally substituted C$_{1-20}$-alkyl, optionally substituted alkenyl preferably optionally substituted C$_{2-12}$-alkenyl, optionally substituted alkynyl preferably optionally substituted C$_{2-12}$-alkynyl, optionally substituted heteroalkyl preferably optionally substituted C$_{2-12}$-heteroalkyl, or optionally substituted cycloalkyl preferably optionally substituted C$_{5-8}$-cycloalkyl;

R$^1$ and R$^2$ are each independently chosen from the group consisting of hydrogen, optionally substituted alkyl preferably optionally substituted C$_{1-20}$-alkyl, optionally substituted alkenyl preferably optionally substituted C$_{2-12}$-alkenyl, optionally substituted alkynyl preferably optionally substituted C$_{2-12}$-alkynyl, optionally substituted heteroalkyl preferably optionally substituted C$_{2-12}$-heteroalkyl, and optionally substituted alkoxy preferably optionally substituted C$_{1-12}$-alkoxy;

n and m are non-negative integers;

n+m is about 5 to about 2000;

m:n is between about 1:100 to about 100:1;

Z is chosen from the group consisting of —C(O)—, —C(O)NH—, —C(OH)HCH$_2$—, and —C(CH$_2$OH)H—; and Y is optionally substituted alkyl preferably optionally substituted C$_{1-20}$-alkyl, optionally substituted alkenyl preferably optionally substituted C$_{2-20}$-alkenyl, optionally substituted alkynyl preferably optionally substituted C$_{2-20}$-alkynyl, optionally substituted heteroalkyl preferably optionally substituted C$_{2-20}$-heteroalkyl, or optionally substituted cycloalkyl preferably optionally substituted C$_{5-8}$-cycloalkyl, —(CH$_2$)$_a$—{O(CH$_2$)$_a$}$_b$ where a is between about 1 and about 7 and b is between about 1 and about 100, optionally substituted aryl or optionally substituted heteroaryl.

The biodegradable polymers according to formula IV are biodegradable and biocompatible before and upon biodegredation.

Additional preferred biodegradable polymers according to formula IV include polymers wherein:

x is 2;

L is —(CH$_2$)$_a$—{O(CH$_2$)$_a$}$_b$ where a is between about 1 and about 7 and b is between about 1 and about 500;

Y is C$_{1-20}$-alkyl, C$_{2-20}$-alkenyl, C$_{2-20}$-alkynyl, or aryl;

Z is —C(O)— or —C(O)NH—;

R is C$_{1-6}$-alkyl; and,

R$^1$ and R$^2$ are independently selected at each occurrence from the group consisting of hydrogen, methyl and ethyl.

Additional preferred biodegradable polymers according to formula IV include polymers wherein:

x is 2;

L is —(CH$_2$)$_a$—{O(CH$_2$)$_a$}$_b$ where a is between about 1 and about 7 and b is between about 1 and about 500;

Y is C$_{1-20}$-alkyl, C$_{2-20}$-alkenyl, C$_{2-20}$-alkynyl, or aryl;

Z is —C(O)— or —C(O)NH—;

R is methyl or ethyl; and,

R$^1$ and R$^2$ are hydrogen.

Biodegradable polymers of the invention according to formula IV include polymers wherein each of m and n is about 10 to 1,000. Preferably each of m and n is about 10 to 500. Moreover, preferred polymers of the invention according to formula IV include polymers wherein the molar ratio, m:n, is between about 1:50 to about 50:1, more preferably between about 1:20 to about 20:1 and particularly preferably between about 1:5 and 5:1.

A preferred biodegradable polymer of the invention comprises repeat units as in formula V:

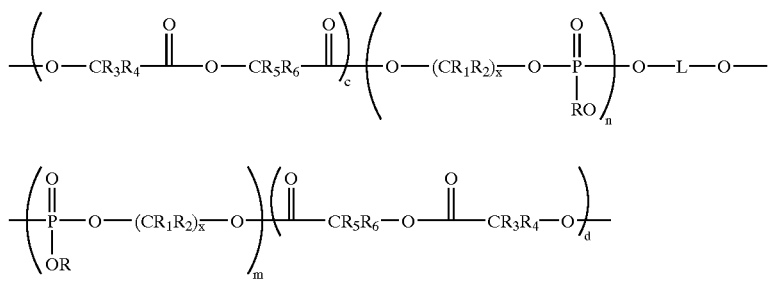

wherein
L is optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-20}$-heteroalkyl, $-(CH_2)_a-\{O(CH_2)_a\}_b$ where a is between about 1 and about 7 and b is between about 1 and about 500, optionally substituted aryl, or optionally substituted heteroaryl;

x is 2, 3, or 4;

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-20}$-heteroalkyl, or optionally substituted cycloalkyl preferably optionally substituted $C_{5-8}$-cycloalkyl;

$R^1$ and $R^2$ are each independently chosen from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl, and optionally substituted alkoxy preferably optionally substituted $C_{1-12}$-alkoxy;

n and m are non-negative integers;

n+m is about 5 to about 2000;

m:n is between about 1:100 to about 100:1;

c and d are non-negative integers;

c+d is about 5 to about 2000; and (m+n):(c+d) is between about 1:100 and 100:1.

The biodegradable polymers according to formula V are biodegradable and biocompatible before and upon biodegradation.

Additional preferred biodegradable polymers according to formula V include polymers wherein:

x is 2;

L is $-(CH_2)_a-\{O(CH_2)_a\}_b$ where a is between about 1 and about 7 and b is between about 1 and about 500;

R is $C_{1-6}$-alkyl;

$R^1$ and $R^2$ are independently selected at each occurrence from the group consisting of hydrogen, methyl and ethyl;

$R^3$ and $R^5$ are hydrogen;

$R^4$ is hydrogen or $C_{1-6}$-alkyl; and, $R^6$ is $C_{1-6}$-alkyl.

Additional preferred biodegradable polymers according to formula V include polymers wherein:

x is 2;

L is $-(CH_2)_a-\{O(CH_2)_a\}_b$ where a is between about 1 and about 7 and b is between about 1 and about 500;

R is methyl or ethyl;

$R^4$ and $R^6$ are methyl; and, $R^1$, $R^2$, $R^3$ and $R^5$ are hydrogen.

Biodegradable polymers of the invention according to formula V include polymers wherein each of c, d, m and n is about 10 to 1,000. Preferably each of c, d, m and n is about 10 to 500 and more preferably each is about 10 to about 200. Moreover, preferred polymers of the invention according to formula V include polymers wherein the molar ratio (c+d):(m+n) is between about 1:50 to 50:1, more preferably between about 1:20 to about 20:1 and particularly preferably between about 1:5 and 5:1.

The invention also includes a process for preparing a biodegradable polymer according to formula I:

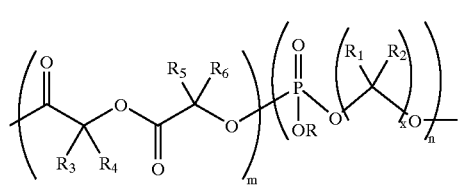

wherein:

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;

$R^1$ and $R^2$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted $C_{1-12}$-alkoxy;

x is 2, 3, or 4;

n and m are non-negative integers;

n+m is about 5 to about 2000; and m:n is between about 1:100 to about 100:1;

wherein the process comprising the steps of:
contacting at least one glycolide derivative and at least one cyclic phosphate; and
polymerizing the glycolide derivative and the cyclic phosphate under conditions conducive to preparing the biodegradable polymer.

Another preferred process of the invention for preparing a polymer according to formula I wherein the glycolide derivative is a compound according to formula VI:

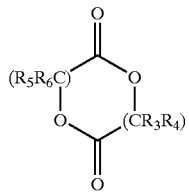

VI $R^4$ and $R^6$ are independently selected from the group consisting of hydrogen, $C_{1-12}$-alkyl, $C_{2-12}$-alkenyl, $C_{2-12}$-alkynyl, and $C_{1-12}$-alkoxy such that both $R^4$ and $R^6$ are not hydrogen; and $R^3$ and $R^5$ are hydrogen.

Another preferred process of the invention for preparing a polymer according to formula I wherein $R^4$ and $R^6$ are methyl.

Another preferred process of the invention for preparing a polymer according to formula I wherein the cyclic phosphate is a compound according to formula VII:

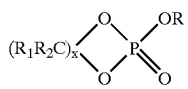

VII wherein
R, independently selected at each occurrence from the group consisting of, optionally substituted $C_{1-12}$-alkyl, optionally substituted $C_{2-12}$-alkenyl, optionally substituted $C_{2-12}$-alkynyl, and optionally substituted $C_{1-12}$-alkoxy;

$R^1$ and $R^2$ are independently selected at each occurrence from the group consisting of hydrogen, optionally substituted $C_{1-12}$-alkyl, optionally substituted $C_{2-12}$-alkenyl, optionally substituted $C_{2-12}$-alkynyl, and optionally substituted $C_{1-12}$-alkoxy; and x is 2, 3 or 4.

Another preferred process of the invention for preparing a polymer according to formula I wherein:
R is methyl;
$R^1$ and $R^2$ are hydrogen at each occurrence of $R^1$ and $R^2$; and,
x is 2.

Preferred processes of the invention for preparing a polymer according to formula I include processes wherein a catalyst is present during the contacting step. Preferred catalysts include aluminum complexes such as trialkoxy aluminum, trialkyl aluminum and the like, zinc complexes such as dialkoxy zinc, diaryloxy zinc, diamido zinc, dialkyl zinc and the like, dicarboxylate tin(II) such as tin(II)bis(2-octanoate) and the like, (beta-diimidate)zinc carboxylate complexes as disclosed in Coates G. W., et al *Journal of the American Chemical Society* (1999) pg 11018 (incorporated herein by reference) and organometallic and metal-alkoxide complexes of other metals such as calcium, magnesium, cadmium, mercury, gallium, boron, copper, nickel and the like.

The invention also includes a process for preparing a biodegradable polymer according to formula III:

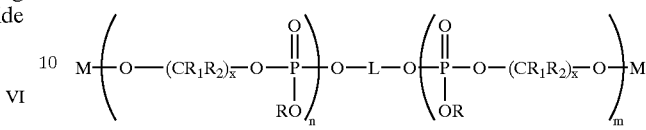

III wherein:
R is hydrogen, optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted alkyl preferably optionally substituted $C_{1-12}$-alkyl;

$R^1$ and $R^2$ are each independently chosen at each occurrence from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

L is chosen from the group consisting of optionally substituted alkyl preferably optionally substituted $C_{2-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl or —$(CH_2)_a$—{O—$(CH_2)_a$}$_b$—, wherein each a is 1–6 and b is 1–500;

n and m are non-negative integers;
n+m is about 5 to about 2000;
x is 2, 3 or 4; and
M is independently chosen at each occurrence of M from the group consisting of H, Na, Li, and K;

the process comprising the steps of:
contacting at least one cyclic phosphate with an initiator compound, HO—L—OH;
polymerizing the cyclic phosphate with the initiator compound under conditions conducive to preparing the biodegradable polymer.

In preferred embodiments of the invention, the process for preparing polymers according to formula III involve the ring opening of cyclic phosphates according to formula VII:

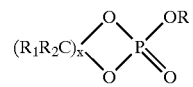

VII wherein
R is hydrogen, $C_{2-12}$-alkenyl, $C_{2-12}$-alkynyl, or $C_{1-12}$-alkyl;

$R^1$ and $R^2$ are independently selected at each occurrence from the group consisting of hydrogen, $C_{1-12}$-alkyl, $C_{2-12}$-alkenyl, $C_{2-12}$-alkynyl, and $C_{1-12}$-alkoxy; and x is 2, 3 or 4.

A more preferred cyclic phosphate according to formula VII is where:

R is methyl or ethyl;

$R^1$ and $R^2$ are hydrogen at each occurrence of $R^1$ and $R^2$; and, x is 2.

Preferred initiator compositions, M—O—L—O—M, include substances wherein M is Li, Na or K.

The invention also includes a process for preparing a biodegradable polymer according to formula IV:

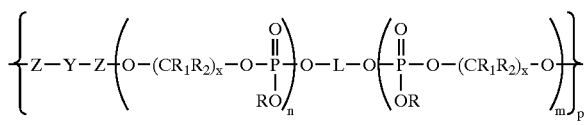

IV wherein

L is optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, —$(CH_2)_a$—$\{O(CH_2)_a\}_b$ where a is between about 1 and about 7 and b is between about 1 and about 500, optionally substituted aryl, or optionally substituted heteroaryl;

x is 2, 3, or 4;

R is hydrogen, optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, or optionally substituted cycloalkyl preferably optionally substituted $C_{5-8}$-cycloalkyl;

$R^1$ and $R^2$ are each independently chosen from the group consisting of hydrogen, optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, and optionally substituted alkoxy preferably optionally substituted $C_{1-12}$-alkoxy;

n and m are non-negative integers;

n+m is about 5 to about 2000;

m:n is between about 1:100 to about 100:1;

Z is chosen from the group consisting of —C(O)—, —C(O)NH—, —C(OH)HCH$_2$—, and —C(CH$_2$OH)H—; and Y is optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{2-20}$-heteroalkyl, or optionally substituted cycloalkyl preferably optionally substituted $C_{5-8}$-cycloalkyl, —$(CH_2)_a$—$\{O(CH_2)_a\}_b$ where a is between about 1 and about 7 and b is between about 1 and about 100, optionally substituted aryl or optionally substituted heteroaryl; and, the process comprising the steps of:

making the biodegradable polymer of claim 13;

contacting the biodegradable polymer of claim 13 with a compound with two functional groups capable of reacting with an alcohol to form a covalent bond; and polymerizing the biodegradable polymer and the compound with two functional groups capable of reacting with an alcohol under conditions conducive to preparing the biodegradable polymer according to formula IV.

In preferred embodiments, the process for preparing a polymer according to formula IV wherein L is —$(CH_2)_2$—$\{O$—$(CH_2)_2\}_b$— and b is 1–50.

In preferred embodiments of the invention, processes to prepare polymers according to formula IV involve a macromolecular monomer according to formula III:

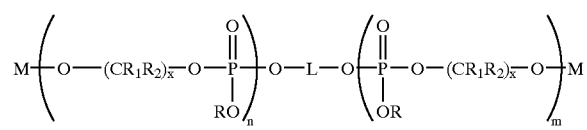

III wherein

R is hydrogen, optionally substituted $C_{2-12}$-alkenyl, optionally substituted $C_{2-12}$-alkynyl, or optionally substituted $C^{1-12}$-alkyl;

$R^1$ and $R^2$ are each independently chosen at each occurrence from the group consisting of hydrogen, optionally substituted $C_{1-12}$-alkyl, optionally substituted $C_{2-12}$-alkenyl, optionally substituted $C_{2-12}$-alkynyl, and optionally substituted $C_{1-12}$-alkoxy;

L is chosen from the group consisting of optionally substituted $C_{2-20}$-alkyl, optionally substituted $C_{2-12}$-alkenyl, optionally substituted $C_{2-12}$-alkynyl, or —$(CH_2)_a$—$\{O$—$(CH_2)_a\}_b$—, wherein each a is 1–6 and b is 1–500;

n and m are non-negative integers;

n+m is about 5 to about 2000;

x is 2, 3 or 4; and

M is hydrogen.

In others preferred embodiments of the invention, processes to prepare polymers according to formula IV involve an A—Y—A compound with two functional groups, A, where A is capable of reacting with an alcohol and Y is $C_{1-20}$-alkyl, $C_{2-12}$-alkenyl, $C_{2-12}$-alkynyl, $C_{5-8}$cycloalkyl, —$(CH_2)_a$—$\{O(CH_2)_a\}_b$ where a is between about 1 and about 7 and b is between about 1 and about 100, aryl or heteroaryl. Preferred A groups include acid halides such as —C(O)C and —C(O)Br, isocyanates (—NCO), epoxides, sulfonyl chlorides (—SO$_2$C), vinyl ethers and other functional groups that react with alcohols to form a covalent bond. See for example, Jerry March, "*Advanced Organic Chemistry*" 4$^{th}$ ed., 1992 and Carey and Sundberg, "*Advanced Organic Chemistry, Part B: Reactions and Synthesis*" 3$^{rd}$ ed., 1990.

The invention also includes a process for preparing a biodegradable polymer according to formula V:

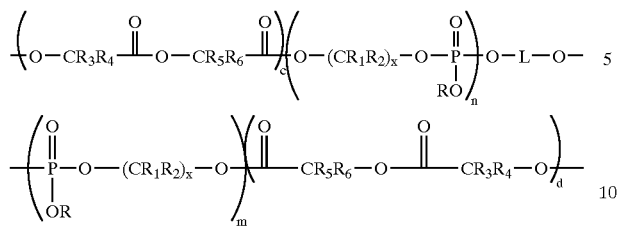

wherein
L is optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-20}$-heteroalkyl, —$(CH_2)_a${—$O(CH_2)_a$}$_b$ where a is between about 1 and about 7 and b is between about 1 and about 500, optionally substituted aryl, or optionally substituted heteroaryl;

x is 2, 3, or 4;

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-20}$-heteroalkyl, or optionally substituted cycloalkyl preferably optionally substituted $C_{5-8}$-cycloalkyl;

$R^1$ and $R^2$ are each independently chosen from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl, and optionally substituted alkoxy preferably optionally substituted $C_{1-12}$-alkoxy;

n and m are non-negative integers;

n+m is about 5 to about 2000;

m:n is between about 1:100 to about 100:1;

c and d are non-negative integers;

c+d is about 5 to about 2000;

(m+n):(c+d) is between about 1:100 and 100:1; and, the process comprising the steps of:

making at least one biodegradable polymer of claim 13;

contacting the biodegradable polymer of claim 13 with at least one glycolide derivative; and polymerizing the glycolide derivative under conditions conducive to the preparing a biodegradable polymer according to formula V.

In more preferred embodiments, the process results in polymers according to formula V, wherein:

x is 2;

L is —$(CH_2)_a$—{$O(CH_2)_a$}$_b$ where a is between about 1 and about 7 and b is between about 1 and about 500;

R is $C_{1-6}$-alkyl;

$R^1$ and $R^2$ are independently selected at each occurrence from the group consisting of hydrogen, methyl and ethyl;

$R^3$ and $R^5$ are hydrogen;

$R^4$ is hydrogen or $C_{1-6}$-alkyl; and, $R^6$ is $C_{1-6}$-alkyl.

In particularly preferred embodiments, the process results in polymers according to formula V, wherein:

x is 2;

L is —$(CH_2)_a$—{$O(CH_2)_a$}$_b$ where a is between about 1 and about 7 and b is between about 1 and about 500;

R is methyl or ethyl;

$R^4$ and $R^6$ are methyl; and, $R^1$, $R^2$, $R^3$ and $R^5$ are hydrogen.

Preferred processes utilize a glycolide derivative according to the formula VI:

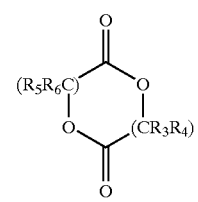

VI wherein:

$R^4$ and $R^6$ are independently selected from the group consisting of hydrogen, $C_{1-12}$-alkyl, $C_{2-12}$-alkenyl, $C_{2-12}$-alkynyl, and $C_{1-12}$-alkoxy such that both $R^4$ and $R^6$ are not hydrogen; and $R^3$ and $R^5$ are hydrogen.

Another preferred process of the invention for preparing a polymer according to formula I wherein $R^4$ and $R^6$ are methyl.

The present invention also relates to a biodegradable polymer composition comprising:

(a) at least one biologically active substance; and (b) a biodegradable polymer comprising at least one repeat unit according to formula A:

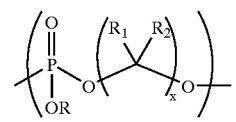

A wherein

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;

$R^1$ and $R^2$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

x is 2, 3, or 4; and at least one repeat unit selected from the group consisting of optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl, —O(CR$_1$R$_2$)$_c$C(O)— where c is between about 1 and about 10, —(CH$_2$)$_a$—{O(CH$_2$)$_a$}$_b$— where a is between about 1 and about 7 and b is be about 1 and about 500, optionally substituted aryl, and optionally substituted heteroaryl; or at least one repeat unit according to formula B:

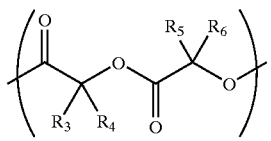

B wherein
R$^3$, R$^4$, R$^5$ and R$^6$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy.

Preferred polymer compositions include a polymer according to formula I:

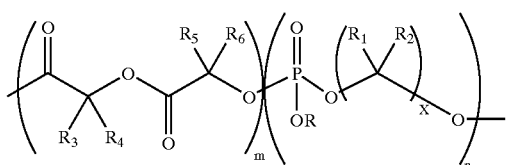

I wherein
R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;
R$^1$ and R$^2$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted $C_{1-12}$-alkoxy;
x is 2, 3, or 4;
n and m are non-negative integers;
n+m is about 5 to about 2000; and
m:n is between about 1:100 to about 100:1.

In preferred embodiments the biodegradable polymer according to formula I is biocompatible before and upon biodegradation.

More preferable are polymer composition according to formula I, wherein
x is 2;
R is methyl or ethyl;
R$^4$ and R$^6$ are methyl; and,
R$^1$, R$^2$, R$^3$ and R$^5$ are hydrogen.

Preferred polymer compositions include a polymer according to formula III:

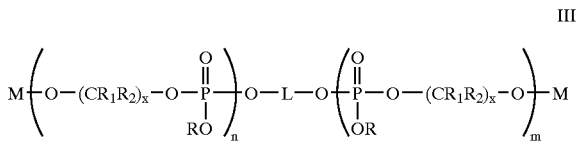

III wherein
R is hydrogen, optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted alkyl preferably optionally substituted $C_{1-12}$-alkyl;
R$^1$ and R$^2$ are each independently chosen at each occurrence from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;
L is chosen from the group consisting of optionally substituted alkyl preferably optionally substituted $C_{2-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl or —(CH$_2$)$_a$—{O—(CH$_2$)$_a$}$_b$—, wherein each a is 1–6 and b is 1–500;
n and m are non-negative integers;
n+m is about 5 to about 2000;
x is 2, 3 or 4; and
M is independently chosen at each occurrence of M from the group consisting of H, Na, Li, and K.

In preferred embodiments, the biodegradable polymer according to formula III are biocompatible before and upon biodegradation.

More preferable are polymer composition according to formula III, wherein
L is —(CH$_2$)$_a$—{O(CH$_2$)$_a$}$_b$ where a is between about 1 and about 7 and b is between about 1 and about 500;
x is 2;
R is methyl or ethyl; and,
R$^1$ and R$^2$ are hydrogen.

Preferred polymer compositions include a polymer according to formula IV:

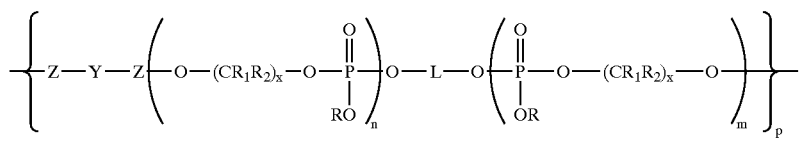

IV wherein
- L is optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, $(CH_2)_a$—$\{O(CH_2)_a\}_b$ where a is between about 1 and about 7 and b is between about 1 and about 500, optionally substituted aryl, or optionally substituted heteroaryl;
- x is 2, 3, or 4;
- R is hydrogen, optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, or optionally substituted cycloalkyl preferably optionally substituted $C_{5-8}$-cycloalkyl;
- $R^1$ and $R^2$ are each independently chosen from the group consisting of hydrogen, optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, and optionally substituted alkoxy preferably optionally substituted $C_{1-12}$-alkoxy;
- n and m are non-negative integers;
- n+m is about 5 to about 2000;
- m:n is between about 1:100 to about 100:1;
- Z is chosen from the group consisting of —C(O)—, —C(O)NH—, —C(OH)HCH$_2$—, and —C(CH$_2$OH)H—; and
- Y is optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{2-20}$-heteroalkyl, or optionally substituted cycloalkyl preferably optionally substituted $C_{5-8}$-cycloalkyl, —(CH$_2$)$_a$—$\{O(CH_2)_a\}_b$ where a is between about 1 and about 7 and b is between about 1 and about 100, optionally substituted aryl or optionally substituted heteroaryl.

In preferred embodiments, the biodegradable polymer according to formula IV is biocompatible before and upon biodegredation.

More preferable are polymer composition according to formula IV, wherein:
- x is 2;
- L is —(CH$_2$)$_a$—$\{O(CH_2)_a\}_b$ where a is between about 1 and about 7 and b is between about 1 and about 500;
- Y is $C_{1-20}$-alkyl, or aryl;
- Z is —C(O)— or —C(O)NH—;

R is methyl or ethyl; and,
$R^1$ and $R^2$ are hydrogen.

Preferred polymer compositions include a polymer according to formula V:

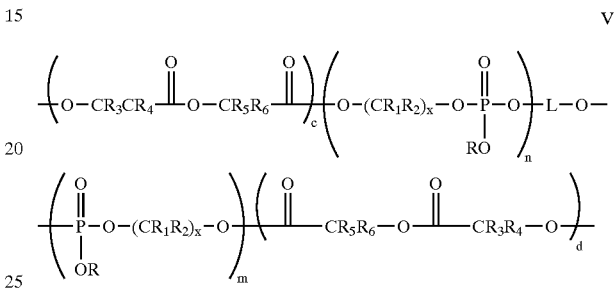

V wherein
- L is optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-20}$-heteroalkyl, —(CH$_2$)$_a$—$\{O(CH_2)_a\}_b$ where a is between about 1 and about 7 and b is between about 1 and about 500, optionally substituted aryl, or optionally substituted heteroaryl;
- x is 2, 3, or 4;
- R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-20}$-heteroalkyl, or optionally substituted cycloalkyl preferably optionally substituted $C_{5-8}$-cycloalkyl;
- $R^1$ and $R^2$ are each independently chosen from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl, and optionally substituted alkoxy preferably optionally substituted $C_{1-12}$-alkoxy;
- n and m are non-negative integers;
- n+m is about 5 to about 2000;
- m:n is between about 1:100 to about 100:1;
- c and d are non-negative integers;
- c+d is about 5 to about 2000; and
- (m+n):(c+d) is between about 1:100 and 100:1.

In preferred embodiments, the biodegradable polymer according to formula V is biocompatible before and upon biodegradation.

More preferable are polymer composition according to formula V, wherein:

x is 2;

L is —(CH$_2$)$_a$—{O(CH$_2$)$_a$}$_b$ where a is between about 1 and about 7 and b is between about 1 and about 500;

R is methyl or ethyl;

R$^4$ and R$^6$ are methyl; and,

R$^1$, R$^2$, R$^3$ and R$^5$ are hydrogen.

The present invention also relates to an article useful for implantation, injection, or otherwise being placed totally or partially within a body, the article comprising a biodegradable polymer composition comprising:

(a) at least one biologically active substance; and (b) a biodegradable polymer comprising at least one repeat unit according to formula A:

$$\left( \begin{matrix} O \\ \| \\ P \\ | \\ OR \end{matrix} - O - \begin{pmatrix} R_1 & R_2 \\ & \\ & \end{pmatrix}_x - O \right)$$

A wherein

R is hydrogen, optionally substituted alkyl preferably optionally substituted C$_{1-12}$-alkyl, optionally substituted alkenyl preferably optionally substituted C$_{2-12}$-alkenyl, optionally substituted alkynyl preferably optionally substituted C$_{2-12}$-alkynyl, optionally substituted heteroalkyl preferably optionally substituted C$_{1-12}$-heteroalkyl or optionally substituted cycloalkyl preferably optionally substituted C$_{5-8}$-cycloalkyl;

R$^1$ and R$^2$ are each independently chosen from the group consisting of H, optionally substituted alkyl preferably optionally substituted C$_{1-12}$-alkyl, optionally substituted alkenyl preferably optionally substituted C$_{2-12}$-alkenyl, optionally substituted alkynyl preferably optionally substituted C$_{2-12}$-alkynyl, optionally substituted heteroalkyl preferably optionally substituted C$_{1-12}$-heteroalkyl and optionally substituted alkoxy preferably optionally substituted C$_{1-12}$-alkoxy;

x is 2, 3, or 4; and at least one repeat unit selected from the group consisting of optionally substituted alkyl preferably optionally substituted C$_{1-20}$-alkyl, optionally substituted alkenyl preferably optionally substituted C$_{2-20}$-alkenyl, optionally substituted alkynyl preferably optionally substituted C$_{2-20}$-alkynyl, optionally substituted heteroalkyl preferably optionally substituted C$_{1-12}$-heteroalkyl, —O(CR$_1$R$_2$)$_c$C(O)— where c is between about 1 and about 10, —(CH$_2$)$_a$—{O(CH$_2$)$_a$}$_b$— where a is between about 1 and about 7 and b is between about 1 and about 500, optionally substituted aryl, and optionally substituted heteroaryl; or at least one repeat unit according to formula B:

B $$\left( \begin{matrix} O \\ \| \\ & \\ R_3 & R_4 \end{matrix} - O - \begin{pmatrix} R_5 & R_6 \\ & \\ & O \end{pmatrix} \right)$$

wherein

R$^3$, R$^4$, R$^5$ and R$^6$ are each independently chosen from the group consisting of H, optionally substituted alkyl preferably optionally substituted C$_{1-12}$-alkyl, optionally substituted alkenyl preferably optionally substituted C$_{2-12}$-alkenyl, optionally substituted alkynyl preferably optionally substituted C$_{2-12}$-alkynyl, optionally substituted heteroalkyl preferably optionally substituted C$_{1-12}$-heteroalkyl and optionally substituted alkoxy preferably optionally substituted C$_{1-12}$-alkoxy.

In preferred embodiments, the biodegradable polymer is biocompatible before and upon biodegradation.

Preferred articles of the invention include a polymer according to formula I:

I $$\left( \begin{matrix} O \\ \| \\ & \\ R_3 & R_4 \end{matrix} - O - \begin{pmatrix} R_5 & R_6 \\ & \\ & O \end{pmatrix} \right)_m \left( \begin{matrix} O \\ \| \\ P \\ | \\ OR \end{matrix} - O - \begin{pmatrix} R_1 & R_2 \\ & \\ & \end{pmatrix}_x - O \right)_n$$

wherein

R is hydrogen, optionally substituted alkyl preferably optionally substituted C$_{1-12}$-alkyl, optionally substituted alkenyl preferably optionally substituted C$_{2-12}$-alkenyl, optionally substituted alkynyl preferably optionally substituted C$_{2-12}$-alkynyl, optionally substituted heteroalkyl preferably optionally substituted C$_{1-12}$-heteroalkyl or optionally substituted cycloalkyl preferably optionally substituted C$_{5-8}$-cycloalkyl;

R$^1$ and R$^2$ are each independently chosen from the group consisting of H, optionally substituted alkyl preferably optionally substituted C$_{1-12}$-alkyl, optionally substituted alkenyl preferably optionally substituted C$_{2-12}$-alkenyl, optionally substituted alkynyl preferably optionally substituted C$_{2-12}$-alkynyl, optionally substituted heteroalkyl preferably optionally substituted C$_{1-12}$-heteroalkyl and optionally substituted C$_{1-12}$-alkoxy;

x is 2, 3, or 4;

n and m are non-negative integers;

n+m is about 5 to about 2000; and m:n is between about 1:100 to about 100:1.

In preferred embodiments, the biodegradable polymer according to Formula I is biocompatible before and upon biodegradation.

More preferable are articles with a polymer component according to formula I, wherein x is 2;

R is methyl or ethyl;

R$^4$ and R$^6$ are methyl; and,

R$^1$, R$^2$, R$^3$ and R$^5$ are hydrogen.

Preferred articles of the invention include a polymer according to formula III:

III $$M\left( O-(CR_1R_2)_x-O-\overset{\overset{O}{\|}}{\underset{\underset{RO}{|}}{P}}-O \right)_n O-L-O\left( \overset{\overset{O}{\|}}{\underset{\underset{OR}{|}}{P}}-O-(CR_1R_2)_x-O \right)_m M$$

wherein

R is hydrogen, optionally substituted C$_{2-12}$-alkenyl, optionally substituted alkynyl preferably optionally substituted C$_{2-12}$-alkynyl, optionally substituted heteroalkyl preferably optionally substituted C$_{1-12}$- heteroalkyl or optionally substituted alkyl preferably optionally substituted $C_{1-12}$-alkyl;

$R^1$ and $R^2$ are each independently chosen at each occurrence from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

L is chosen from the group consisting of optionally substituted alkyl preferably optionally substituted $C_{2-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl or —$(CH_2)_a$—$\{O—(CH_2)_a\}_b$—, wherein each a is 1–6 and b is 1–500;

n and m are non-negative integers;

n+m is about 5 to about 2000;

x is 2, 3 or 4; and

M is independently chosen at each occurrence of M from the group consisting of H, Na, Li, and K.

More preferable are articles with a polymer component according to formula III, wherein L is —$(CH_2)_a$—$\{O(CH_2)_a\}_b$ where a is between about 1 and about 7 and b is between about 1 and about 500;

x is 2;

R is methyl or ethyl; and, $R^1$ and $R^2$ are hydrogen.

Preferred articles of the invention include a polymer according to formula IV:

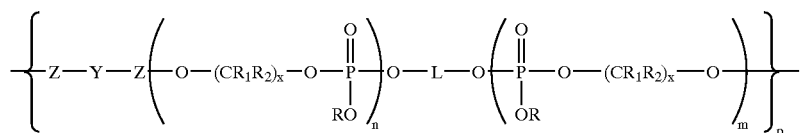

wherein

L is optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, —$(CH_2)_a$—$\{O(CH_2)_a\}_b$ where a is between about 1 and about 7 and b is between about 1 and about 500, optionally substituted aryl, or optionally substituted heteroaryl;

x is 2, 3, or 4;

R is hydrogen, optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, or optionally substituted cycloalkyl preferably optionally substituted $C_{5-8}$-cycloalkyl;

$R^1$ and $R^2$ are each independently chosen from the group consisting of hydrogen, optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, and optionally substituted alkoxy preferably optionally substituted $C_{1-12}$-alkoxy;

n and m are non-negative integers;

n+m is about 5 to about 2000;

m:n is between about 1:100 to about 100:1;

Z is chosen from the group consisting of —C(O)—, —C(O)NH—, —C(OH)HCH$_2$—, and —C(CH$_2$OH)H—; and Y is optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{2-20}$-heteroalkyl, or optionally substituted cycloalkyl preferably optionally substituted $C_{5-8}$-cycloalkyl, —$(CH_2)_a$—$\{O(CH_2)_a\}_b$ where a is between about 1 and about 7 and b is between about 1 and about 100, optionally substituted aryl or optionally substituted heteroaryl.

In preferred embodiments, the biodegradable polymer according to formula IV is biocompatible before and upon biodegredation.

More preferable are articles with a polymer component according to formula IV, wherein:

x is 2;

L is —$(CH_2)_a$—$\{O(CH_2)_a\}_b$ where a is between about 1 and about 7 and b is between about 1 and about 500;

Y is $C_{1-20}$-alkyl, $C_{2-20}$-alkenyl, $C_{2-20}$-alkynyl, or aryl;

Z is —C(O)— or —C(O)NH—;

R is methyl or ethyl; and, $R^1$ and $R^2$ are hydrogen.

Preferred articles of the invention include a polymer according to formula V:

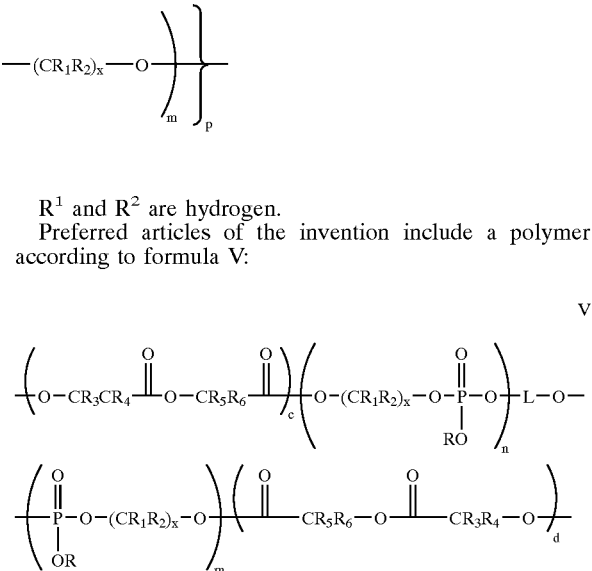

wherein

L is optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-20}$-heteroalkyl, —$(CH_2)_a$—$\{O(CH_2)_a\}_b$ where a is between about 1 and about 7 and b is between about 1 and about 500, optionally substituted aryl, or optionally substituted heteroaryl;

x is 2, 3, or 4;

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-20}$-heteroalkyl, or optionally substituted cycloalkyl preferably optionally substituted $C_{5-8}$-cycloalkyl;

$R^1$ and $R^2$ are each independently chosen from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl, and optionally substituted alkoxy preferably optionally substituted $C_{1-12}$-alkoxy;

n and m are non-negative integers;

n+m is about 5 to about 2000;

m:n is between about 1:100 to about 100:1;

c and d are non-negative integers;

c+d is about 5 to about 2000; and (m+n):(c+d) is between about 1:100 and 100:1.

In preferred embodiments, the biodegradable polymer according to formula V is biocompatible before and upon biodegradation.

More preferable are articles with a polymer component according to formula V, wherein:

x is 2;

L is —$(CH_2)_a$—$\{O(CH_2)_a\}_b$ where a is between about 1 and about 7 and b is between about 1 and about 500;

R is methyl or ethyl;

$R^4$ and $R^6$ are methyl; and, $R^1$, $R^2$, $R^3$ and $R^5$ are hydrogen.

The present invention also relates to methods for the controlled release of at least one biologically active substance comprising the steps of:

(a) combining the biologically active substance with a biodegradable polymer comprising at least one repeat unit according to formula A:

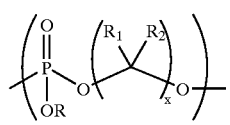

A wherein

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;

$R^1$ and $R^2$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

x is 2, 3, or 4; and at least one repeat unit selected from the group consisting of optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-20}$-alkynyl, optionally substituted heteroalkyl preferably optionally substituted $C_{1-12}$-heteroalkyl, —$O(CR_1R_2)_cC(O)$— where c is between about 1 and about 10, —$(CH_2)_a$—$\{(CH_2)_a\}_b$— where a is between about 1 and about 7 and b is between about 1 and about 500, optionally substituted aryl, and optionally substituted heteroaryl; or at least one repeat unit according to formula B:

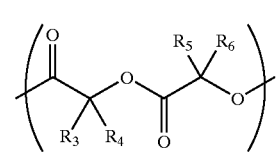

B wherein $R^3$, $R^4$, $R^5$ and $R^6$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

to form an admixture;

(b) forming said admixture into a shaped, solid article or microsphere; and (c) implanting or injecting the solid article or microsphere in vivo at a preselected site, such that the solid implanted or injected matrix is in at least partial contact with a biological fluid.

Preferred methods of the invention include a polymer according to formula I:

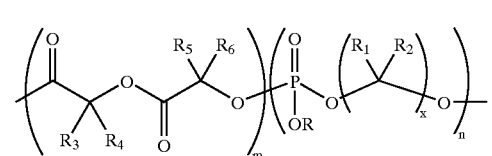

I wherein

R is hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted cycloalkyl preferably optionally substituted $C_{5-8}$-cycloalkyl;

$R^1$ and $R^2$ are each independently chosen from the group consisting of H, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted $C_{1-12}$-alkoxy;

x is 2, 3, or 4;

n and m are non-negative integers;

n+m is about 5 to about 2000; and m:n is between about 1:100 to about 100:1.

In preferred embodiments, the biodegradable polymer according to formula I is biocompatible before and upon biodegredation.

More preferable are methods with a polymer component according to formula I, wherein:

x is 2;

R is methyl or ethyl;

$R^4$ and $R^6$ are methyl; and, $R^1$, $R^2$, $R^3$ and $R^5$ are hydrogen.

Preferred methods include a polymer according to formula III:

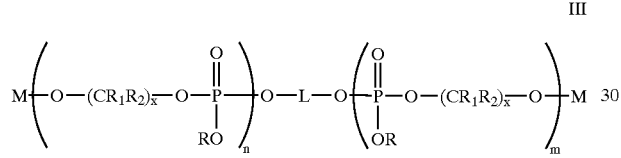

wherein

R is hydrogen, optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl or optionally substituted alkyl preferably optionally substituted $C_{1-12}$-alkyl;

$R^1$ and $R^2$ are each independently chosen at each occurrence from the group consisting of hydrogen, optionally substituted alkyl preferably optionally substituted $C_{1-12}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{1-12}$-heteroalkyl and optionally substituted alkoxy preferably optionally substituted $C_{1-12}$-alkoxy;

L is chosen from the group consisting of optionally substituted alkyl preferably optionally substituted $C_{2-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{1-12}$-heteroalkyl or —$(CH_2)_a$—$\{O-(CH_2)_a\}_b$—, wherein each a is 1–6 and b is 1–500;

n and m are non-negative integers;

n+m is about 5 to about 2000;

x is 2, 3 or 4; and

M is independently chosen at each occurrence of M from the group consisting of H, Na, Li, and K.

In preferred embodiments, the biodegradable polymer according to formula III is biocompatible before and upon biodegradation.

More preferable are methods with a polymer component according to formula III, wherein:

L is —$(CH_2)_a$—$\{O(CH_2)_a\}_b$ where a is between about 1 and about 7 and b is between about 1 and about 500;

x is 2;

R is methyl or ethyl; and, $R^1$ and $R^2$ are hydrogen.

Preferred methods include a polymer according to formula IV:

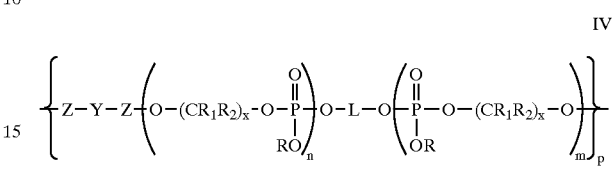

wherein

L is optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, —$(CH_2)_a$—$\{O(CH_2)_a\}_b$ where a is between about 1 and about 7 and b is between about 1 and about 500, optionally substituted aryl, or optionally substituted heteroaryl;

x is 2, 3, or 4;

R is hydrogen, optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, or optionally substituted cycloalkyl preferably optionally substituted $C_{5-8}$-cycloalkyl;

$R^1$ and $R^2$ are each independently chosen from the group consisting of hydrogen, optionally substituted alkyl preferably optionally substituted $C_{1-20}$-alkyl, optionally substituted alkenyl preferably optionally substituted $C_{2-12}$-alkenyl, optionally substituted alkynyl preferably optionally substituted $C_{2-12}$-alkynyl, optionally substituted heteroalkyl preferably optionally substituted $C_{2-12}$-heteroalkyl, and optionally substituted alkoxy preferably optionally substituted $C_{1-12}$-alkoxy;

n and m are non-negative integers;

n+m is about 5 to about 2000;

m:n is between about 1:100 to about 100:1;

Z is chosen from the group consisting of —C(O)—, —C(O)NH—, —C(OH)HCH$_2$—, and —C(CH$_2$OH)H—; and Y is optionally substituted alkyl preferably optionally substituted $C_{1-20}$-alkyl, optionally substituted alkenyl preferably optionally substituted $C_{2-20}$-alkenyl, optionally substituted alkynyl preferably optionally substituted $C_{2-20}$-alkynyl, optionally substituted heteroalkyl preferably optionally substituted $C_{2-20}$-heteroalkyl, or optionally substituted cycloalkyl preferably optionally substituted $C_{5-8}$-cycloalkyl, —$(CH_2)_a$—$\{O(CH_2)_a\}_b$ where a is between about 1 and about 7 and b is between about 1 and about 100, optionally substituted aryl or optionally substituted heteroaryl.

In preferred embodiments, the biodegradable polymer according to formula IV is biocompatible before and upon biodegredation.

More preferable are methods with a polymer component according to formula IV, wherein:

x is 2;

L is —(CH$_2$)$_a$—{O(CH$_2$)$_a$}$_b$ where a is between about 1 and about 7 and b is between about 1 and about 500;

Y is C$_{1-20}$-alkyl, C$_{2-20}$-alkenyl, C$_{2-20}$-alkynyl, or aryl;

Z is —C(O)— or —C(O)NH—;

R is methyl or ethyl; and,

R$^1$ and R$^2$ are hydrogen.

Preferred methods include a polymer according to formula V:

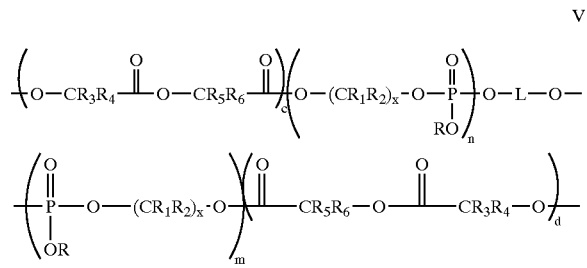

V wherein

L is optionally substituted alkyl preferably optionally substituted C$_{1-20}$-alkyl, optionally substituted alkenyl preferably optionally substituted C$_{2-20}$-alkenyl, optionally substituted alkynyl preferably optionally substituted C$_{2-20}$-alkynyl, optionally substituted heteroalkyl preferably optionally substituted C$_{1-20}$-heteroalkyl, —(CH$_2$)$_a$—{O(CH$_2$)$_a$}$_b$ where a is between about 1 and about 7 and b is between about 1 and about 500, optionally substituted aryl, or optionally substituted heteroaryl;

x is 2, 3, or 4;

R is hydrogen, optionally substituted alkyl preferably optionally substituted C$_{1-12}$-alkyl, optionally substituted alkenyl preferably optionally substituted C$_{2-12}$-alkenyl, optionally substituted alkynyl preferably optionally substituted C$_{2-12}$-alkynyl, optionally substituted heteroalkyl preferably optionally substituted C$_{1-20}$-heteroalkyl, or optionally substituted cycloalkyl preferably optionally substituted C$_{5-8}$-cycloalkyl;

R$^1$ and R$^2$ are each independently chosen from the group consisting of hydrogen, optionally substituted alkyl preferably optionally substituted C$_{1-12}$-alkyl, optionally substituted alkenyl preferably optionally substituted C$_{2-12}$-alkenyl, optionally substituted alkynyl preferably optionally substituted C$_{2-12}$-alkynyl, optionally substituted heteroalkyl preferably optionally substituted C$_{1-12}$-heteroalkyl, and optionally substituted alkoxy preferably optionally substituted C$_{1-12}$-alkoxy;

n and m are non-negative integers;

n+m is about 5 to about 2000;

m:n is between about 1:100 to about 100:1;

c and d are non-negative integers;

c+d is about 5 to about 2000; and (m+n):(c+d) is between about 1:100 and 100:1.

In preferred embodiments, the biodegradable polymer according to formula V is biocompatible before and upon biodegradation.

More preferable are methods with a polymer component according to formula V, wherein:

x is 2;

L is —(CH$_2$)$_a$—{O(CH$_2$)$_a$}$_b$ where a is between about 1 and about 7 and b is between about 1 and about 500;

R is methyl or ethyl;

R$^4$ and R$^6$ are methyl; and,

R$^1$, R$^2$, R$^3$ and R$^5$ are hydrogen.

As indicated above, various substituents of the various formulae are "optionally substituted", including Ar, R$_1$, R$_2$, and R$_3$ of Formula I, and such substituents as recited in the sub-formulae such as Formulae Ia and the like. When substituted, those substituents (Ar, R$_1$, R$_2$, and R$_3$) may be substituted by other than hydrogen at one or more available positions, typically 1 to 3 or 4 positions, by one or more suitable groups such as those disclosed herein. Suitable groups that may be present on a "substituted" Ar, R$_1$, R$_2$, and R$_3$ group or other substituent include e.g. halogen such as fluoro, chloro, bromo and iodo; cyano; hydroxyl; nitro; azido; alkanoyl such as a C$_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups having those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons, particularly phenyl (e.g. an Ar group being a substituted or unsubstituted biphenyl moiety); aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

As used herein, "alkyl" is intended to include branched, straight-chain and cyclic saturated aliphatic hydrocarbon groups including alkylene, having the specified number of carbon atoms. Examples of alkyl include, but are not limited to, methyl, ethyl, n-propyl, i-propyl, n-butyl, s-butyl, t-butyl, n-pentyl, and s-pentyl. Alkyl groups typically have 1 to about 16 carbon atoms, more typically 1 to about 20 or 1 to about 12 carbon atoms. Preferred alkyl groups are C$_1$–C$_{20}$ alkyl groups, more preferred are C$_{1-12}$-alkyl and C$_{1-6}$-alkyl groups. Especially preferred alkyl groups are methyl, ethyl, and propyl.

As used herein, "heteroalkyl" is intended to include branched, straight-chain and cyclic saturated aliphatic hydrocarbon groups including alkylene, having the specified number of carbon atoms and at least one heteroatom, e.g., N, O or S. Heteroalkyl groups will typically have between about 1 and about 20 carbon atoms and about 1 to about 8 heteroatoms, preferably about 1 to about 12 carbon atoms and about 1 to about 4 heteroatoms. Preferred heteroalkyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alylthio groups having 1, 2, 3, or 4 carbon atoms are particularly preferred. Preferred alkylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkylsulfinyl groups having 1, 2, 3, or 4 carbon atoms are particularly preferred. Preferred alkylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alylsulfonyl groups having 1, 2, 3, or 4 carbon atoms are particularly preferred. Preferred aminoalkyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkyl groups having 1, 2, 3, or 4 carbon atoms are particularly preferred.

As used herein, "heteroalkenyl" is intended to include branched, straight-chain and cyclic saturated aliphatic hydrocarbon groups including alkenylene, having the specified number of carbon atoms and at least one heteroatom, e.g., N, O or S. Heteroalkenyl groups will typically have between about 1 and about 20 carbon atoms and about 1 to about 8 heteroatoms, preferably about 1 to about 12 carbon atoms and about 1 to about 4 heteroatoms. Preferred heteroalkenyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alkenylthio groups having 1, 2, 3, or 4 carbon atoms are particularly preferred. Prefered alkenylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkenylsulfinyl groups having 1, 2, 3, or 4 carbon atoms are particularly preferred. Preferred alkenylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkenylsulfonyl groups having 1, 2, 3, or 4 carbon atoms are particularly preferred. Preferred aminoalkenyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkenyl groups having 1, 2, 3, or 4 carbon atoms are particularly preferred.

As used herein, "heteroalkynyl" is intended to include branched, straight-chain and cyclic saturated aliphatic hydrocarbon groups including alkynylene, having the specified number of carbon atoms and at least one heteroatom, e.g., N, O or S. Heteroalkynyl groups will typically have between about 1 and about 20 carbon atoms and about 1 to about 8 heteroatoms, preferably about 1 to about 12 carbon atoms and about 1 to about 4 heteroatoms. Preferred heteroalkynyl groups include the following groups. Preferred alkynylthio groups include those groups having one or more thioether linkages and from 1 to about 12 carbon atoms, more preferably from 1 to about 8 carbon atoms, and still more preferably from 1 to about 6 carbon atoms. Alkynylthio groups having 1, 2, 3, or 4 carbon atoms are particularly preferred. Prefered alkynylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkynylsulfinyl groups having 1, 2, 3, or 4 carbon atoms are particularly preferred. Preferred alkynylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkynylsulfonyl groups having 1, 2, 3, or 4 carbon atoms are particularly preferred. Preferred aminoalkynyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkynyl groups having 1, 2, 3, or 4 carbon atoms are particularly preferred.

As used herein, "cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "($C_{3-6}$ cycloalkyl)$C_{1-4}$ alkyl", as defined above, the point of attachment is on the alkyl group. This term encompasses, but is not limited to, cyclopropylmethyl, cyclohexylmethyl, cyclohexylmethyl.

As used here, "alkenyl" is intended to include hydrocarbon chains of straight, cyclic or branched configuration, including alkenylene, and one or more unsaturated carbon-carbon bonds which may occur in any stable point along the chain, such as ethenyl and propenyl. Alkenyl groups typically will have 2 to about 12 carbon atoms, more typically 2 to about 12 carbon atoms.

As used herein, "alkynyl" is intended to include hydrocarbon chains of straight, cyclic or branched configuration, including alkynylene, and one or more triple carbon-carbon bonds which may occur in any stable point along the chain, such as ethynyl and propynyl. Alkynyl groups typically will have 2 to about 20 carbon atoms, more typically 2 to about 12 carbon atoms.

As used herein, "haloalkyl" is intended to include both branched and straight-chain saturated aliphatic hydrocarbon groups having the specified number of carbon atoms, substituted with 1 or more halogen (for example $-C_vF_w$ where v=1 to 3 and w=1 to (2v+1). Examples of haloalkyl include, but are not limited to, trifluoromethyl, trichloromethyl, pentafluoroethyl, and pentachloroethyl. Typical haloalkyl groups will have 1 to about 16 carbon atoms, more typically 1 to about 12 carbon atoms.

As used herein, "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 16 carbon atoms, more typically 1 to about 12 carbon atoms.

As used herein, "Lewis acid catalysts" represents the standard synthetic chemistry definition thereof. Moreover a Lewis acid is a compound or composition that acts as an electron pair acceptor. Typical Lewis acid catalysts include aluminum alkoxide complexes such as $Al(OR)_3$ where R is alkyl or aryl, borates such as $BF_3$ or $B(OR)_3$, titanium alkoxides and titanium halides, zinc complexes such as zinc halides, alkoxides, carboxylates, amides and the like, particularly $Zn(OR)_2$ and $Zn(NR_2)_2$ where R is alkyl, aryl or trialkylsilyl and tin complexes, particularly tin(II) complexes such as Stannous chloride, tin alkoxides and tin carboxylates. Particularly preferred Lewis acid catalysts include $Al(O^iPr)_3$, $Al(OPh)_3$, $Zn(N(SiMe_3)_2)_2$, $Zn(OPh)_2$, $B(OPh)_3$, $B(OC_6F_5)_3$, $Sn(II)(O_2CC_8H_{17})_2$ and like complexes.

"Prodrugs" are intended to include any covalently bonded carriers which release the active parent drug according to formula I in vivo when such prodrug is administered to a mammalian subject. Prodrugs of a compound are prepared by modifying functional groups present in the drug compound in such a way that the modifications are cleaved, either in routine manipulation or in vivo, to the parent compound.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent.

As used herein, the term "aliphatic" refers to a linear, branched, cyclic alkane, alkene, or alkyne. Preferred aliphatic groups in the poly(phosphoester-co-amide) polymer of the invention are linear or branched and have from 1 to 20 carbon atoms.

As used herein, the term "aryl" refers to an unsaturated cyclic carbon compound with $4n+2\pi$ a electrons where n is a non-negative integer, about 5–18 aromatic ring atoms and about 1 to about 3 aromatic rings.

As used herein, the term "heterocyclic" refers to a saturated or unsaturated ring compound having one or more atoms other than carbon in the ring, for example, nitrogen, oxygen or sulfur.

Biodegradable polymers differ from non-biodegradable polymers in that they can be degraded during in vivo therapy. This generally involves breaking down the polymer into its monomeric subunits. In principle, the ultimate hydrolytic breakdown products of a polymer of the invention are one or more alpha-hydroxyacids, an aliphatic alcohol or alkanediol, and phosphate. In certain embodiments, the ultimate hydrolytic breakdown products of a polymer according to formulae III, IV or V may further comprise poly(ethyleneglycol) and the like. All of these degradation products are potentially non-toxic. However, the intermediate oligomeric products of the hydrolysis may have different properties. Thus, toxicology of a biodegradable polymer intended for implantation or injection, even one synthesized from apparently innocuous monomeric structures, is typically determined after one or more toxicity analyses.

A typical in vitro toxicity assay would be performed with live carcinoma cells, such as GT3TKB tumor cells, in the following manner:

200 µL of various concentrations of suspensions of the test monomer or polymers are placed in 96-well tissue culture plates seeded with human gastric carcinoma cells (GT3TKB) at 10. sup.4/well density. The degraded polymer products are incubated with the GT3TKB cells for 48 hours. The results of the assay can be plotted as % relative growth vs. concentration of degraded polymer in the tissue-culture well.

Polymers for use in medical applications such as implants and prostheses can also be evaluated by well-known in vivo tests, such as subcutaneous implantations in rats to confirm that they hydrolyze without significant levels of irritation or inflammation at the subcutaneous implantation sites.

The biodegradable polymer of the invention is preferably sufficiently pure to be biocompatible itself and remains biocompatible upon biodegradation. By "biocompatible" is meant that the biodegradation products or the polymer itself are nontoxic and result in only minimal tissue irritation when implanted or injected into vasculated tissue.

The polymer of the invention is preferably soluble in one or more common organic solvents for ease of fabrication and processing. Common organic solvents include such solvents as ethanol, chloroform, dichloromethane, acetone, ethyl acetate, DMAC, N-methyl pyrrolidone, dimethylformamide, and dimethylsulfoxide. The polymer is preferably soluble in at least one of the above solvents.

The polymer of the invention can also comprise additional biocompatible monomeric units so long as they do not interfere with the biodegradable characteristics desired. Such additional monomeric units may offer even greater flexibility in designing the precise release profile desired for targeted drug delivery or the precise rate of biodegradability desired for structural implants such as for orthopedic applications. Examples of such additional biocompatible monomers include the recurring units found in polycarbonates; polyorthoesters; polyamides; polyurethanes; poly (iminocarbonates); and polyanhydrides.

The process of the invention can take place at widely varying temperatures, depending upon whether a solvent is used and, if so, which one; the molecular weight desired; the susceptibility of the reactants to form side reactions; and the presence of a catalyst. Preferably, however, the process takes place at a temperature ranging from about 0 to about +235° C. for melt conditions. Somewhat lower temperatures, e.g., for example from about −50 to about 100° C. may be possible with solution polymerization or with the use of either a cationic or anionic catalyst.

The time required for the process also can vary widely, depending on the type of reaction being used, the molecular weight desired and, in general, the need to use more or less rigorous conditions for the reaction to proceed to the desired degree of completion. Typically, however, the process takes place during a time between about 30 minutes and 7 days.

While the process may be in bulk, in solution, by interfacial polycondensation, or any other convenient method of polymerization, preferably, the process takes place under solution conditions. Particularly useful solvents include methylene chloride, chloroform, tetrahydrofuran, dimethyl formamide, dimethyl sulfoxide or any of a wide variety of inert organic solvents.

Particularly when solution polymerization reaction is used, an acid acceptor is advantageously present during the polymerization step (a). A particularly suitable class of acid acceptor comprises tertiary amines, such as pyridine, trimethylamine, triethylamine, substituted anilines and substituted aminopyridines. The most preferred acid acceptor is the substituted aminopyridine 4-dimethylaminopyridine ("DMAP").

The polymer of formula I is isolated from the reaction mixture by conventional techniques, such as by precipitating out, extraction with an immiscible solvent, evaporation, filtration, crystallization and the like. Typically, however, the polymer of formula I is both isolated and purified by quenching a solution of polymer with a non-solvent or a partial solvent, such as diethyl ether or petroleum ether.

The polymers of the invention are usually characterized by a release rate of the biologically active substance in vivo that is controlled at least in part as a function of hydrolysis of the phosphoester bond of the polymer during biodegradation. Additionally, the biologically active substance to be released may be conjugated to the phosphorus sidechain R' to form a pendant drug delivery system. Further, other factors are also important.

The life of a biodegradable polymer in vivo also depends upon its molecular weight, crystallinity, biostability, and the degree of cross-linking. In general, the greater the molecular weight, the higher the degree of crystallinity, and the greater the biostability, the slower biodegradation will be.

Accordingly, the structure of the sidechain can influence the release behavior of compositions comprising a biologically active substance. For example, it is expected that conversion of the phosphate sidechain to a more lipophilic, more hydrophobic or bulky group would slow down the degradation process. Thus, release is usually faster from polymer compositions with a small aliphatic group sidechain than with a bulky aromatic sidechain.

The mechanical properties of the polymer are also important with respect to the processability in making molded or pressed articles for implantation. For example, the glass transition temperature can vary widely but must be sufficiently lower than the temperature of decomposition to accommodate conventional fabrication techniques, such as compression molding, extrusion or injection molding. The polymers of the invention typically have glass transition temperatures varying between about 25 to about 750° C. and, preferably, from about 45 to about 65° C.

Weight-average molecular weights (Mw) typically vary from about 2,000 to about 200,000 daltons, preferably from about 2,000 to about 100,000 daltons and, most preferably, from about 2,000 to about 20,000 daltons. Number average molecular weights (Mn) can also vary widely, but generally fall in the range of about 1,000 to 100,000, preferably about 1,000 to 50,000 and, most preferably, from about 1,000 to about 10,000. For controlled release of a substance from a polymer matrix applications, preferred polymers of the invention have a Mw that is directly proportional to the specified length of time over which polymer degradation occurs, e.g., high Mw polymers undergo complete degradation more slowly than low Mw polymers. Preferred polymers of the invention for use in tissue engineering applications and medical device applications, e.g., staples, scalpels and the like preferably have a high Mw and good mechanical properties.

Intrinsic viscosities generally vary from about 0.01 to about 2.0 dL/g in chloroform at 40° C., preferably from about 0.01 to about 1.0 dL/g and, most preferably, about 0.01 to about 0.5 dL/g.

The polymer according to any one of formula I, II, III, IV or V can be used either alone or as a composition containing, in addition, a biologically active substance to form a variety of useful biodegradable materials. For example, the polymer according to any one of formula I, II, III, IV or V can be used to produce a biosorbable suture, an orthopedic appliance or bone cement for repairing injuries to bone or connective tissue, a laminate for degradable or non-degradable fabrics, or a coating for an implantable device, even without the presence of a biologically active substance.

Preferably, however, the biodegradable polymer composition comprises both:
(a) at least one biologically active substance and
(b) a polymer according to any one of formula I, II, III, IV or V.

The biologically active substance of the invention can vary widely with the purpose for the composition. The active substance(s) may be described as a single entity or a combination of entities. The delivery system is designed to be used with biologically active substances having high water-solubility as well as with those having low water-solubility to produce a delivery system that has controlled release rates. The term "biologically active substance" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of useful biologically active substances include the following expanded therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, antigenic materials, and prodrugs.

Specific examples of useful biologically active substances from the above categories include: (a) anti-neoplastics such as androgen inhibitors, antimetabolites, cytotoxic agents, immunomodulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (;) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, anti-virals, antiseptics and antibiotics; and (o) antigenic materials, particularly those useful in vaccine applications.

Preferably, the biologically active substance is selected from the group consisting of polysaccharides, growth factors, hormones, anti-angiogenesis factors, interferons or cytokines, and pro-drugs. In a particularly preferred embodiment, the biologically active substance is a therapeutic drug or pro-drug, most preferably a drug selected from the group consisting of chemotherapeutic agents and other anti-neoplastics, antibiotics, anti-virals, anti-fungals, anti-inflammatories, anticoagulants, an antigenic materials.

The biologically active substances are used in amounts that are therapeutically effective. While the effective amount of a biologically active substance will depend on the particular material being used, amounts of the biologically active substance from about 1% to about 65% have been easily incorporated into the present delivery systems while achieving controlled release. Lesser amounts may be used to achieve efficacious levels of treatment for certain biologically active substances.

In addition, the polymer composition of the invention can also comprise polymer blends of the polymer of the invention with other biocompatible polymers, so long as they do not interfere undesirably with the biodegradable characteristics of the composition. Blends of the polymer of the invention with such other polymers may offer even greater flexibility in designing the precise release profile desired for targeted drug delivery or the precise rate of biodegradability desired for structural implants such as for orthopedic applications. Examples of such additional biocompatible polymers include other polycarbonates; polyesters; polyorthoesters; polyamides; polyurethanes; poly(iminocarbonates); and polyanhiydrides.

Pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and adsorbents in order to prepare a particular medicated composition.

In its simplest form, a biodegradable therapeutic agent delivery system consists of a dispersion of the therapeutic agent in a polymer matrix. The therapeutic agent is typically released as the polymeric matrix biodegrades in vivo into soluble products that can be excreted from the body.

In a particularly preferred embodiment, an article is used for implantation, injection, or otherwise placed totally or partially within the body, the article comprising the biodegradable polymer composition of the invention. The biologically active substance of the composition and the polymer of the invention may form a homogeneous matrix, or the biologically active substance may be encapsulated in some way within the polymer. For example, the biologically active substance may be first encapsulated in a microsphere and then combined with the polymer in such a way that at least a portion of the microsphere structure is maintained. Alternatively, the biologically active substance may be sufficiently immiscible in the polymer of the invention that it is dispersed as small droplets, rather than being dissolved, in the polymer. Either form is acceptable, but it is preferred that, regardless of the homogeneity of the composition, the release rate of the biologically active substance in vivo remain controlled, at least partially as a function of hydrolysis of the phosphoester bond of the polymer upon biodegradation.

In a preferred embodiment, the article of the invention is designed for implantation or injection into the body of an animal. It is particularly important that such an article result in minimal tissue irritation when implanted or injected into vasculated tissue.

As a structural medical device, the polymer compositions of the invention provide a physical form having specific chemical, physical, and mechanical properties sufficient for the application and a composition that degrades in vivo into non-toxic residues. Typical structural medical articles include such implants as orthopedic fixation devices, ventricular shunts, laminates for degradable fabric, drug-carriers, biosorbable sutures, burn dressings, coatings to be placed on other implant devices, and the like.

In orthopedic articles, the composition of the invention may be useful for repairing bone and connective tissue injuries. For example, a biodegradable porous material can be loaded with bone morphogenetic proteins to form a bone graft useful for even large segmental defects. In vascular graft applications, a biodegradable material in the form of woven fabric can be used to promote tissue ingrowth. The polymer composition of the invention may be used as a temporary barrier for preventing tissue adhesion, e.g., following abdominal surgery.

On the other hand, in nerve regeneration articles, the presence of a biodegradable supporting matrix can be used to facilitate cell adhesion and proliferation. When the polymer composition is fabricated as a tube for nerve generation, for example, the tubular article can also serve as a geometric guide for axonal elongation in the direction of functional recovery.

As a drug delivery device, the polymer compositions of the invention provide a polymeric matrix capable of sequestering a biologically active substance and provide predictable, controlled delivery of the substance. The polymeric matrix then degrades to non-toxic residues.

Biodegradable medical implant devices and drug delivery products can be prepared in several ways. The polymer can be melt processed using conventional extrusion or injection molding techniques, or these products can be prepared by dissolving in an appropriate solvent, followed by formation of the device, and subsequent removal of the solvent by evaporation or extraction.

Once a medical implant article is in place, it should remain in at least partial contact with a biological fluid, such as blood, internal organ secretions, mucous membranes, cerebrospinal fluid and the like.

The following examples are illustrative of the invention. All documents mentioned herein are incorporated herein by reference.

Two distinct synthetic pathways for the production of two series of copolymers are disclosed with Example 1 (synthetic scheme of poly(D,L-lactide-coethylene methyl phosphate) and Example 2 (synethetic scheme of elechelic polyphosphate)). Both synthetic pathways are based on the opening of ringed monomers. Properties of the novel copolymers are described. Further, in Example 3 a side chain modification is provided (demethylation of poly (L-lactide-b-ethylene methyl phosphate-b-L-lactide). Further still in vivo drug release from pellets manufactured from three (3) copolymers is presented.

The general schematic of the new polymers and their properties are described below.

EXAMPLE 1

Synthesis of Poly(D,L-lactide-co-ethylene Methyl Phosphate)

Scheme 1
Synthetic scheme of poly(D,L-lactide-co-ethylene methyl phosphate)

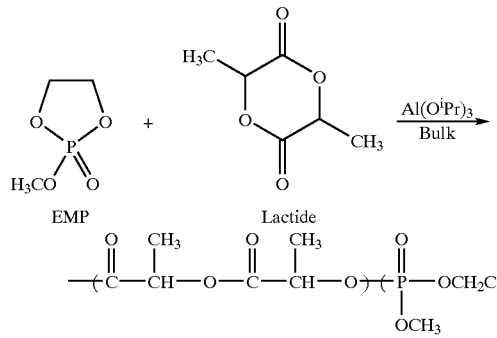

Monomers:

D,L-lactide was purchased from Aldrich and purified by recrystallization from ethyl acetate and sublimation at 70° C. under vacuum. Aluminum isopropoxide (Al(OiPr)3) was prepared from aluminum and dry 2-propanol in the presence of mercuric (II) chloride, and was dissolved in dry toluene before use. Ethylene methyl phosphate was synthesized by Edmundson method with modification as follows:

To a mixture of phosphorus tnchloride (412.5 g, 3 mole) in dry CH2Cl2 (350 mL), ethylene glycol (186 g, 3 mole) was added dropwise over 5 h with vigorous magnetic stirring. Gaseous HCl was evacuated from the reaction flask at reduced pressure (water pump). After complete addition of ethylene glycol, the solution was stirred at room temperature for another 30 min and then solvent was evaporated under reduced pressure. The residue was distilled under vacuum to give 287 g of 0.2-chloro-1,3,2-dioxaphospholane in 75.6% yield (bp. 42aC/1600 Pa). The oxidation of 2-chloro-1,3,2-dioxaphospholane was carried out by bubbling O2 through benzene solution at 50° C. for 24 h. After removal of benzene, the residue was distilled under vacuum to give a colorless liquid of 2-chloro-2-oxo-1,3,2-dioxaphospholane in 85% yield (88–90° C./106 Pa).

A mixture containing a calculated amount of 2-chloro-2-oxo-1,3,2-dioxaphospholane (41.4 g, 0.29 mole) and dry benzene (250 ML) was cooled to –5° C. A mixture of methanol (9.3 g, 0.29 mole) and triethylamine (29.3 g, 0.29 mole) was added dropwise with stirring end cooling. The temperature of the reaction mixture was maintained between –5° C. and 0 C. After complete addition, the resulting mixture was stirred at room temperature for 1.5 h. Triethylamine hydrochloride slat was filtered off and the filtrate was concentrated. The residue was distilled under vacuum to give 28.6 g of 2-methoxy-2-oxo-1,3,2-dioxaphospholane in 71% yield (bp. 99–101° C./106 Pa).

Copolymerization (Scheme 1)

D,L-Lactide and ethylene methyl phosphate (EMP) were copolymerized in bulk under a dry argon atmosphere with Al(OiPr)3 as the initiator. The monomers (in Table 1, the charging molar ratio of D,L-Lactide to EMP was 10) and initiator were introduced to a thoroughly dried vessel. The solvent was removed under vacuum and the vessel purged with argon. The vessel was sealed and immersed in an oil bath at 140–160° C. for 1 to 3 days. The resulting polymers were dissolved in methylene chloride and extracted three times with distilled water and precipitated in hexane. The polymer was obtained as white powder after dried under vacuum.

TABLE 1

Copolymerization of D,L-LA and EMP under different conditions[#]

| Total monomer/initiator (molar ratio) | Temperature (° C.) | Time (h) | Yield (%) | Mn[*] |
|---|---|---|---|---|
| 600 | 160 | 24 | 77 | 11,200 |
| 1,000 | 160 | 24 | 75 | 15,700 |
| 1,500 | 160 | 24 | 71 | 26,500 |
| 1,000 | 160 | 12 | 50 | 7,900 |
| 1,000 | 140 | 24 | 62 | 12,400 |
| 1,000 | 160 | 36 | 78 | 21,700 |

[#]The ratio of D,L-LA to EMP was set to 10.
[*]Mn was measured by vapor pressure osmometry (VPO) using choroform as solvent at 37° C.

Characterization of Copolymers.

(1) Structural Characterization

Figure 2:
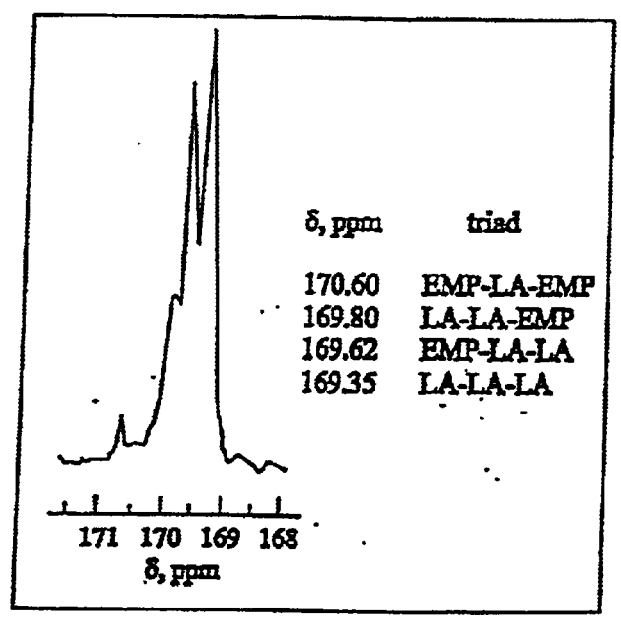
FIG. 2 is an expanded view of a portion of the $^{13}$C-NMR spectrum of poly(D,L-lactide-co-ethylene methyl phosphate) shown in FIG. 1.

The copolymer structures were ascertained by FT-IR, H-NMR and C-NMR (FIG. 1). Some of the signals were split into multiple peaks, due to the random polymerization. For example, the carbonyl signal of lactide in the copolymer appeared as a quadruplet. Their assignment was shown is FIG. 2, which also suggested the random sequences of the copolymer.

(2) Polymer Hydrophilicity

Figure 3:
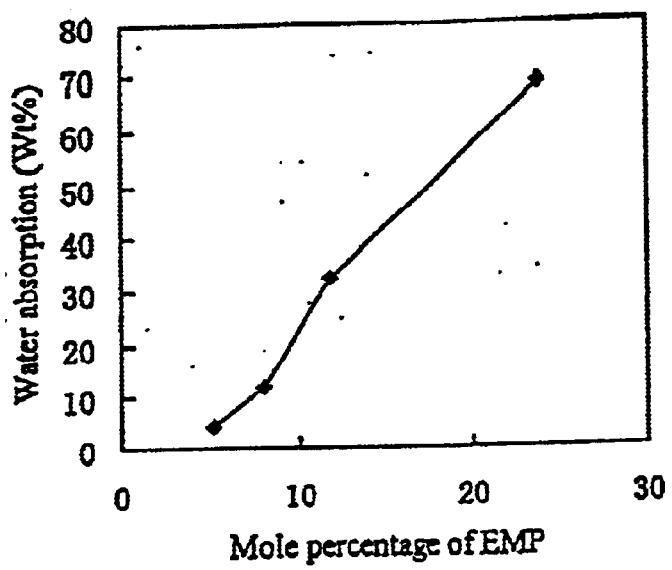
FIG. 3 is a plot of water absorption of poly(D,L-lactide-co-ethylene methyl phosphate) as a function of ethylene methyl phosphate content.

Water absorption of polymer s was defined as the weight percentage of water in wet polymers, after incubated in distilled water to equilibrium at room temperature. A good linear regression was found between the water absorption (hydrophilicity) and EMP fraction in the polymer (FIG. 3).

(3) Thermal Transition

Figure 4:
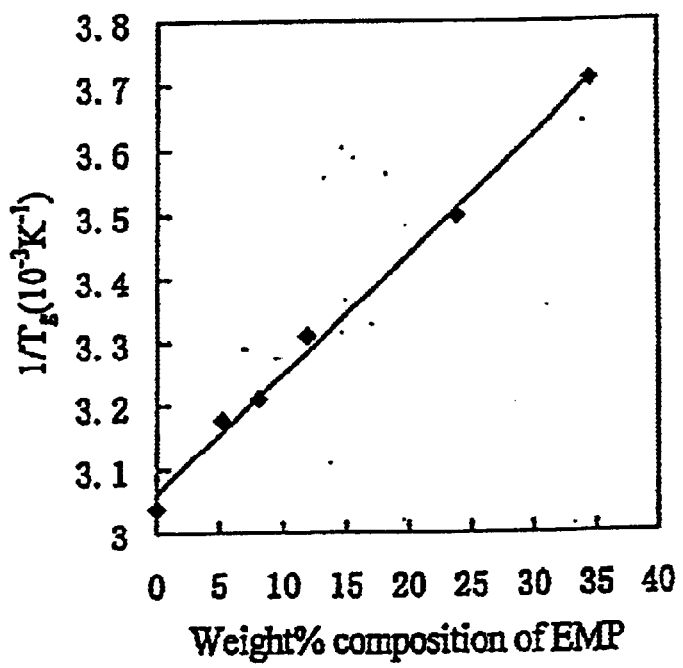
FIG. 4 is a plot of glass transition temperature in ° C. of poly(D,L-lactide-co-ethylene methyl phosphate) as a function of ethylene methyl phosphate content.
Figure 5:
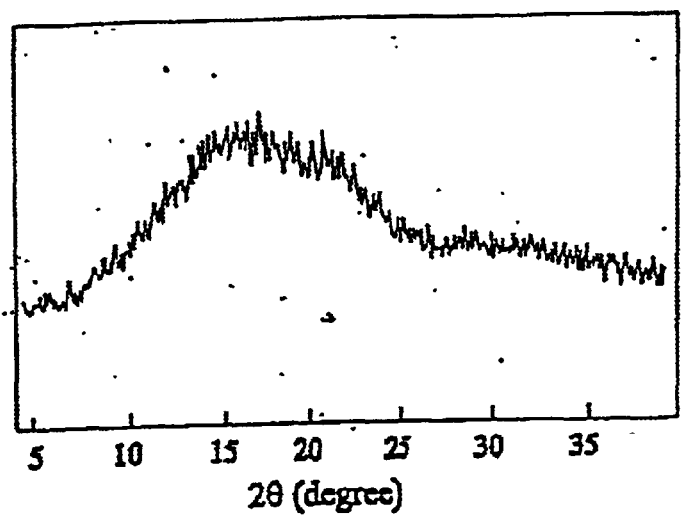
FIG. 5 is a wide angle X-ray diffraction pattern of poly(D,L-lactide-co-ethylene methyl phosphate)

Only one glass transition temperature (Tg) was observed in the Differential Scanning Calorimetry (DSC) graph for all copolymers with different fractions of monomers. Tg decreased with the increase of EMP fraction, and the relationship between Tg and the composition of the copolymers fitted Fox equation very well (FIG. 4). This indicated that the amorphous phase in these copolymers was homogeneous. It was also confirmed by wide angle X-ray diffraction (WAXD) pattern (FIG. 5).

(4) In vitro Degradation

Figure 6:
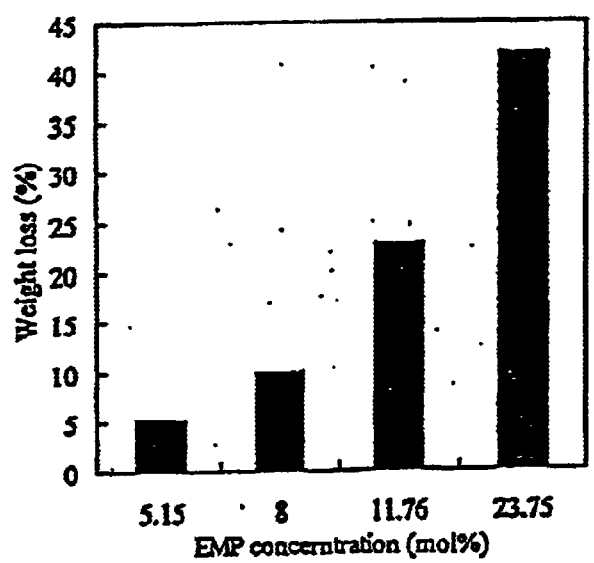
FIG. 6 is a plot of In vitro degradation of poly(D,L-lactide-co-ethylene methyl phosphate) in PBS at 37° C.

Mass loss of disc samples of the copolymers with different EMP fractions was measured in PBS at 37 ac. As expected, polymers with a higher EMP content degraded faster in vitro. A copolymer with 8 mol % of EMP lost about 10% of its original weight in 10 days, whereas copolymer with 23.75% EMP gave about 41% weight loss (FIG. 6).

EXAMPLE 2

Synthesis of Poly(D,L-lactide-b-ethylene Methyl Phosphate-b-D,L-lactide)

Synthesis of Telechelic Polyphosphate (Scheme 2).

Scheme 2
Synthetic scheme of telechelic polyphosphate

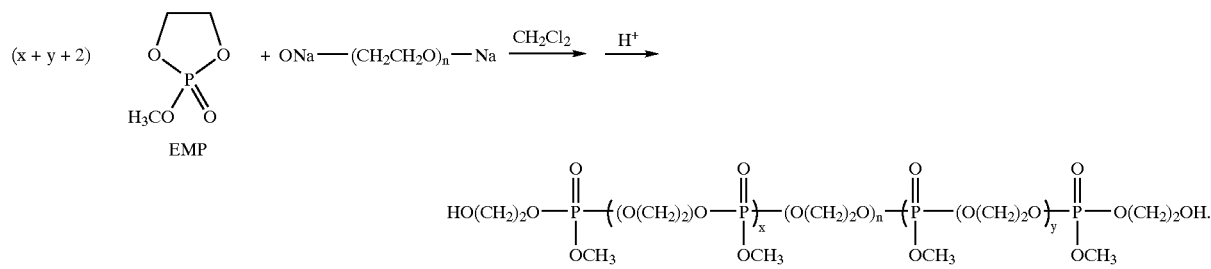

A solution of a,ω dihydroxyl poly(ethylene glycol) (PEG, 2 mmole) and sodium hydride (4.2 mmole) in 20 ml of THF was placed in a dry argon purged vessel equipped with magnetic stirring bar and refluxed condenser. The mixture was stirred at 60° C. for 16 h. The obtained macro-initiator was filtered and sealed until use. Polymerization of EMP was carried out in CH2Cl2 solution at 20° C. under stirring. EMP, methylene chloride and the macro-initiator solution were sequentially introduced into the reactor with syringes through a septum. The mixture was allowed to react for 3 min. The polymerization was terminated by introduction of ten-fold excess of acetic acid (in diethyl ether) with regard to sodium ion. After concentrated, the residue was poured into benzene to give a syrup and then washed with diethyl ether for three times and dried under vacuum to a constant weight.

TABLE 2

Results of the anionic polymerization of EMP initiated with sodium poly(ethylene glycol)ate in CH$_2$Cl$_2$ at 25° C.[a].

| Sample | Yield (%) | Mole Ratio of EO[b] to EMP | | Mn[c] |
|---|---|---|---|---|
| | | Fed | Found | |
| 1 | 95 | 26:74 | 26.4:73.6 | 3000 |
| 2 | 94 | 19:81 | 19.7:80.3 | 4200 |
| 3 | 92 | 12:88 | 12.8:87.2 | 6900 |
| 4 | 96 | 7:93 | 7.3:92.7 | 12500 |

[a]the polymerization time was 3 minutes. [b]EO is ethylene oxide. [c]estimated from $^1$H-NMR spectra (±10% accuracy)

Results of the polymerization are presented in Table 2. The telechelic polymers with the expected molecular weight and composition were obtained in high yields. The block copolymer compositions that calculated from H-NMR spectra were found to be consistent with the charging ratios.

Figure 7:
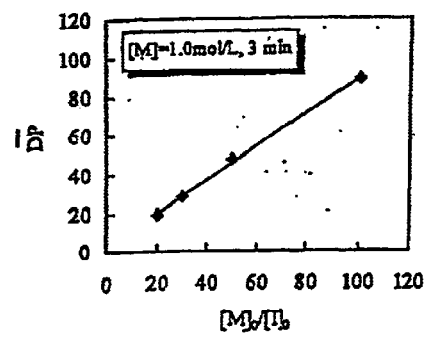
FIG. 7 is a plot of the molecular weight of polyphosphate as a function of monomer to initiator ratio.

The yield and molecular weight of the copolymer reached a peak at 3 min after the reaction started then both decreased and leveled off with increase of the reaction time. A living polymerization characteristic was observed when the polymerization time is within 3 min. This is supported by the linear regression (FIG. 7) between the degree of polymerization and the monomer/initiator molar ratio.

Characterization of Telechelic Polyphosphate

The IR spectra of the polymer showed that the most important and identifying PEMP peaks were $v_{p=O}$ appearing as a sharp singlet at 1269 cm$^{-1}$ and $v_{P-O-C}$ at 1038, 986 cm$^{-1}$. The peak at 110 cm$^{-1}$ was assigned to $v_{C-O-C}$ from PEG segment. Polymers gave a broad absorption peak at the region of 3200–3600 cm$^{-1}$ due to the terminal hydroxyl groups. As expected, the hydroxyl absorption became stronger when the molecular weight of the polymer decreased.

Figure 8:
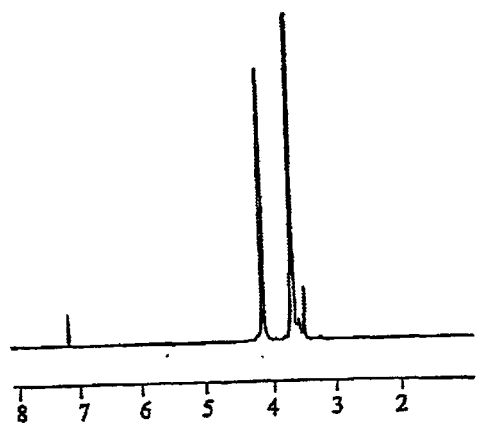
FIG. 8 is a $^1$H-NMR spectrum of polyphosphate diol (EO mol–%=16.3, 3 min.)
Figure 9:
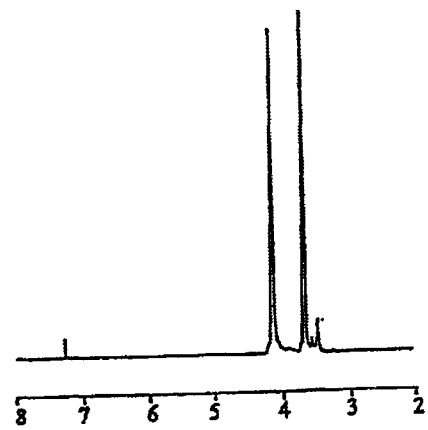
FIG. 9 is a $^1$H{$^{31}$P}-NMR spectrum of polyphosphate diol (EO mol–%=16.3, 3 min.)

The $^1$H NMR and $^1$H{$^{31}$P}-NMR spectra of polyphosphate diol are shown in FIGS. 8 and 9. $^1$H($^{31}$P}-NMR spectrum exhibited, besides signals corresponding to PEG (at δ 3.59 ppm) and PEMP chain [δ4.23 ppm (—CH$_2$OP) and δ 3.77 ppm (CH$_3$OP)], an additional signal at δ 3.67 ppm which was assigned to methylene protons connected to the terminal hydroxyl groups. The $^1$H NMR spectrum gave an expected splitting of a CH$_3$OP singlet into a doublet due to the P—H coupling ($^3$J$_{PH}$=11.25 HZ).

Scheme 3
Synthetic scheme of the block copolymer of poly(L-lactide) and poly(ethylene methyl phophate)

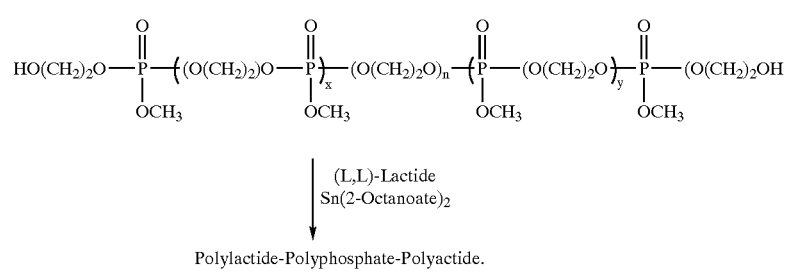

Polylactide-Polyphosphate-Polyactide.

Figure 10:
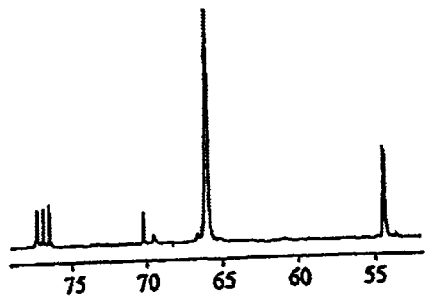
FIG. 10 is a $^{13}$C-NMR spectrum of polyphosphate diol (EO mol–%=16.3, 3 min.)

Additional information about the block structure of polyphosphate was obtained by $^{13}$C NMR studies. FIG. 10 shows the typical $^{13}$C-NMR spectrum of the polymer. In comparison with the spectra of PEG and PEMP, it is clear that peaks at 654.48 ppm and 666.16 ppm correspond to $CH_3$ and $CH_2$ in PEMP segments and the peak at 070.28 belongs to $CH_2$ in PEG segments. Another two small peaks at 066.80 ppm and 069.71 ppm may be due to $POCH_2$ and $CH_2OH$ in the end groups.

Synthesis of the Block Copolymers (Scheme 3)

To a reaction flask, L-lactide and telechelic phosphate (Table 3) were added, and dried under vacuum for 8 hours at room temperature. Under a dry argon stream, the mixture was heated to 120° C. and stirred to reach the homogeneity. After cooled to room temperature, a pre-calculated amount of $Sn(Oct)_2$ was transferred to the flask. The mixture was reacted at 120° C. for desired time (see Table 3). The block copolymers were obtained as white powder after re-precipitating in $CH_2C_{12}$-methol solvent pair, and dried under vacuum.

Characterization of Block Copolymerization.

(1) Structural Characterization

Figure 11A:
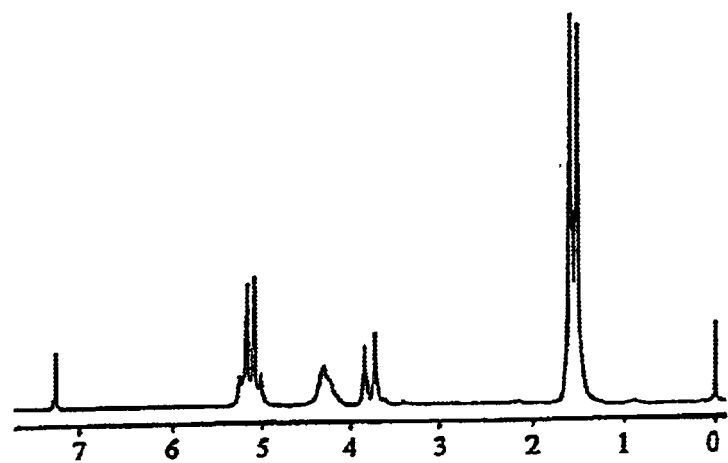
FIG. 11a is a $^1$H-NMR spectrum of DL-lactide and ethylene methyl phosphate block copolymer.
Figure 11B:
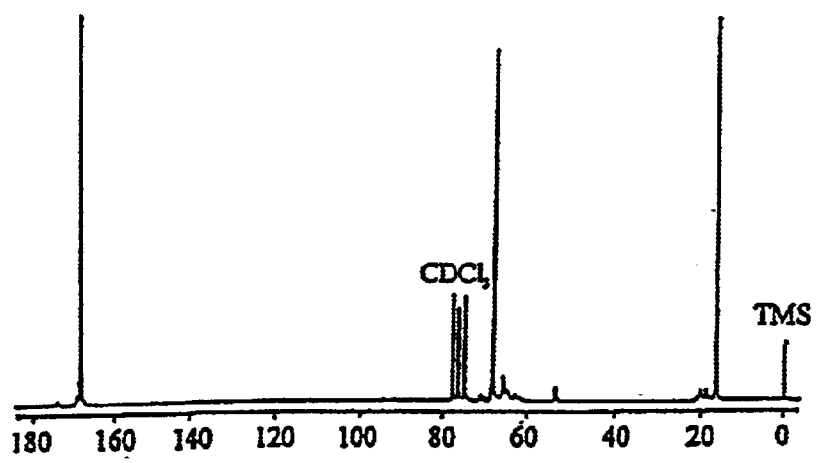
FIG. 11b is a $^{13}$C-NMR spectrum of D,L-lactide and ethylene methyl phosphate block copolymer.

Single peak observed in the Gel Permeation Chromatography (GPC) graphs suggested the formation of the block copolymers. $^1$H-NMR, $^{13}$C-NMR (FIG. 11) and FT-IR confirmed their chemical structures.

found in the DSC graphs, indicating the existence of the crystalline phase (Table 3). Poor compatibility of the two segments-poly(lactide) and poly(phosphate) resulted in the micro-phase separation.

(3) Wide Angle X-ray Diffraction

Figures 12A, 12B, 12C:
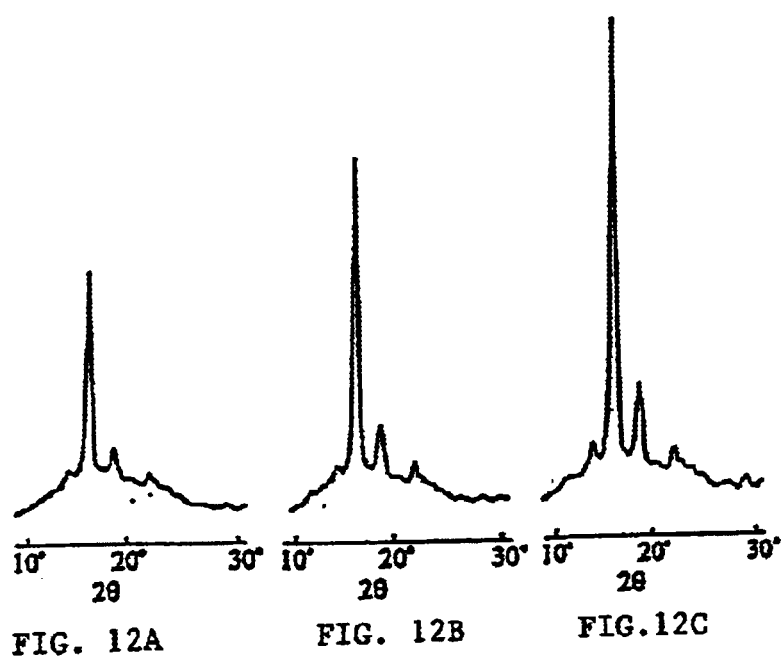
FIG. 12a is a wide angle X-ray diffraction pattern of poly(L-lactide-b-ethylene methyl phosphate-b-L-lactide) with a LA:EMP ratio of 1.8:1.
FIG. 12b is a wide angle X-ray diffraction pattern of poly(L-lactide-b-ethylene methyl phosphate-b-L-lactide) with a LA:EMP ratio of 5.0:1.
FIG. 12c is a wide angle X-ray diffraction pattern of poly(L-lactide-b-ethylene methyl phosphate-b-L-lactide) with a LA:EMP ratio of 15.4:1.

The WAXD diagrams (FIG. 12) of the copolymers showed the same peaks for crystalline poly(L-lactide). This also confirmed the micro-phase separation morphology. The degree of crystallinity decreases with the increase of EMP fraction.

EXAMPLE 3

Side Chain Modification of Poly(L-lactide-b-ethylene Methyl Phosphate-b-L-lactide)

TABLE 3

Synthesis of poly (L-lactide-b-ethylene methyl phosphate-b-L-lactide)

| LA/EMP Feeding | LA/EMP Found | Mn of PEMP | Molar ratio of Lactide/Catalyst | Reaction Time (h) | Yield (%) | Mn of copolymer | Mw/Mn |
|---|---|---|---|---|---|---|---|
| 1.5 | 1.8 | 13,300 | 1,000 | 24 | 81 | 37,700 | N.D. |
| 3.0 | 3.2 | 13,300 | 1,000 | 48 | 83 | 56,700 | 1.35 |
| 5.0 | 5.0 | 13,300 | 2,000 | 72 | 92 | 81,100 | 1.38 |
| 16.0 | 14.5 | 6,100 | 1,000 | 96 | 87 | 99,800 | 1.29 |
| 20 | 16.8 | 6,100 | 1,000 | 168 | 84 | 107,700 | 1.62 |

N.D. means "not determined."

(2) Thermal Transition

Copolymers showed typical block copolymer characteristics. Two glass transition and a clear melting peek were

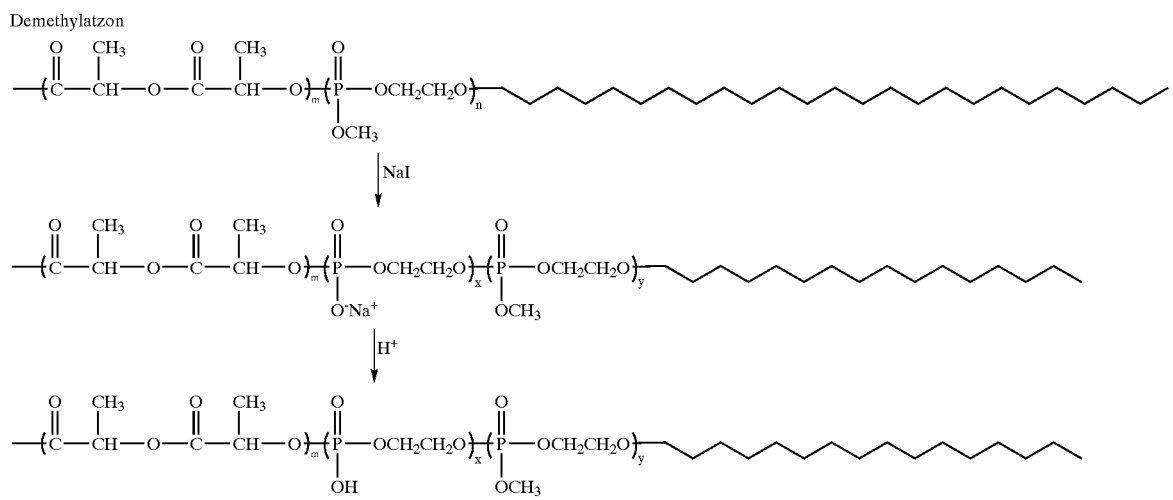

Scheme 4

A copolymer (designated as $I_{14.5}$) with a molar ratio of LA/EMP of 14.5 was used for the demethylation reaction. One half grams of $I_{14.5}$ and 0.1 g of NaI was dissolved in 20 ml of acetone. The solution was refluxed for 5 hours, cooled to room temperature, and acidified with dilute hydrochloric acid. The solution was concentrated into a small volume and poured into distilled water. The white precipitate was collected by filtration, washed with large amount of methanol, and dried under vacuum. The partially demethylated copolymer ($II_{14.5}$) was obtained as white powder with 95% yield.

Figure 13:
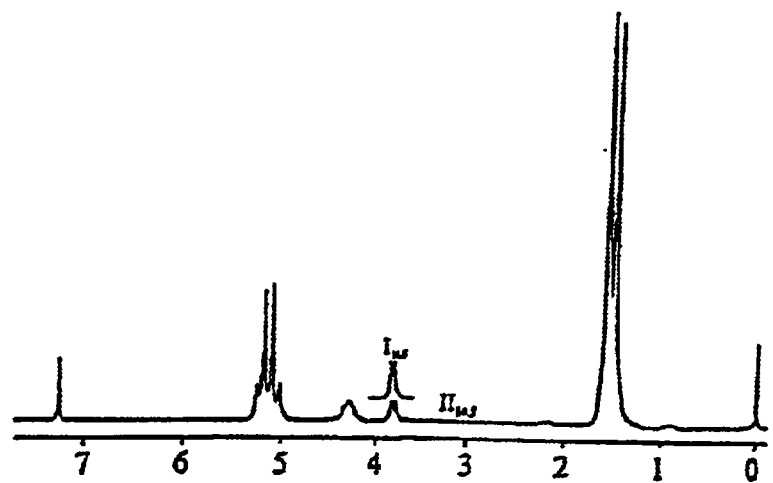
FIG. 13 is a $^1$H-NMR spectrum of demethylated poly(L-lactide-b-ethylene methyl phosphate-b-L-lactide)

The degree of demethylation was accessed by the signal intensify of methoxy group in the $^1$H-NMR spectra (FIG. 13). $II_{14.5}$ has a demethylation degree of about 60%.

In vitro Release of p-nitroaniline.

Pellets that had a diameter of 11 mm, and 3 mm in thickness, with a 6.25% wt. % loading level were fabricated at 500 MPa (room temperature, 15 min.). The pellets were incubated with 120 ml of PBS (pH7.4) at 37° C. The amount of drug released was analyzed at 380 nm by a W spectrophotometer.

Figure 14:
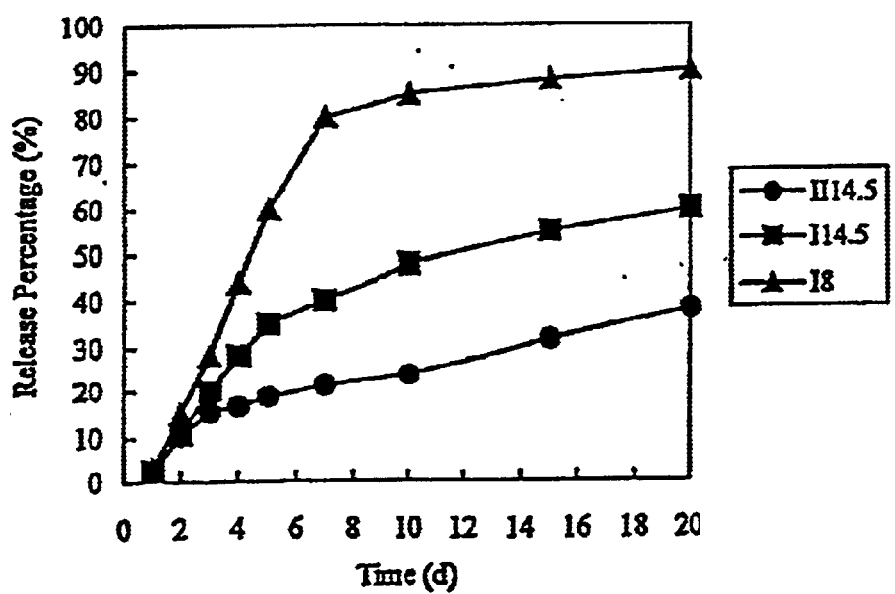
FIG. 14 is an In vitro release of para-nitroaniline through the block copolymers II$_{14.5}$, I$_{14.5}$, and I$_8$ from Table 4.

In vitro release of p-nitroaniline was conducted from three copolymers in these series, $I_{14.5}$, $II_{14.5}$ and $I_6$. The release rate increased with the increase of EMP fraction, which is the result of higher hydrophilicity and lower crystallinity (FIG. 14). Although $II_{14.5}$ was more hydrophilic, the release rate of p-nitroaniline from $II_{14.5}$ was slower than that from $I_{14.5}$. This suggested that :$II_{14.5}$ (a polymeric acid) interacted with the loaded drug, p-nitroaniline (a base) due to the electrostatic interaction, which in turn slowed down the drug release (FIG. 14).

EXAMPLE 4
Synthesis of Poly($\epsilon$-caprolactone-co-ethylene-ethylphosphate)

A random copolymer of poly($\epsilon$-caprolactone-co-ethylene-ethylphosphate) is prepared analogously to the synthesis of poly(lactide-co-ethylene methylphosphate) as in Example 1. A mixture of $\epsilon$-caprolactone and ethylene-ethylphosphate in the presence of Al(O$^i$Pr)$_3$ in a melt polymerization (scheme 5). The ratio of monomer repeat units in the resulting poly($\epsilon$-caprolactone-co-ethylene-ethylphosphate) can be controlled by varying the relative ratio of monomers in the melt.

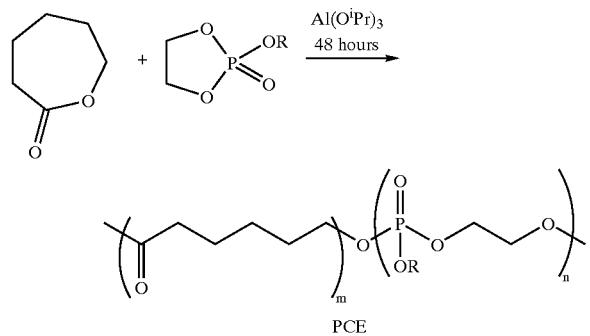

Scheme 5

PCE

EXAMPLE 5
Cytotoxicity of Poly(lactide-co-ethylene Ethylphosphate)

Figure 15:
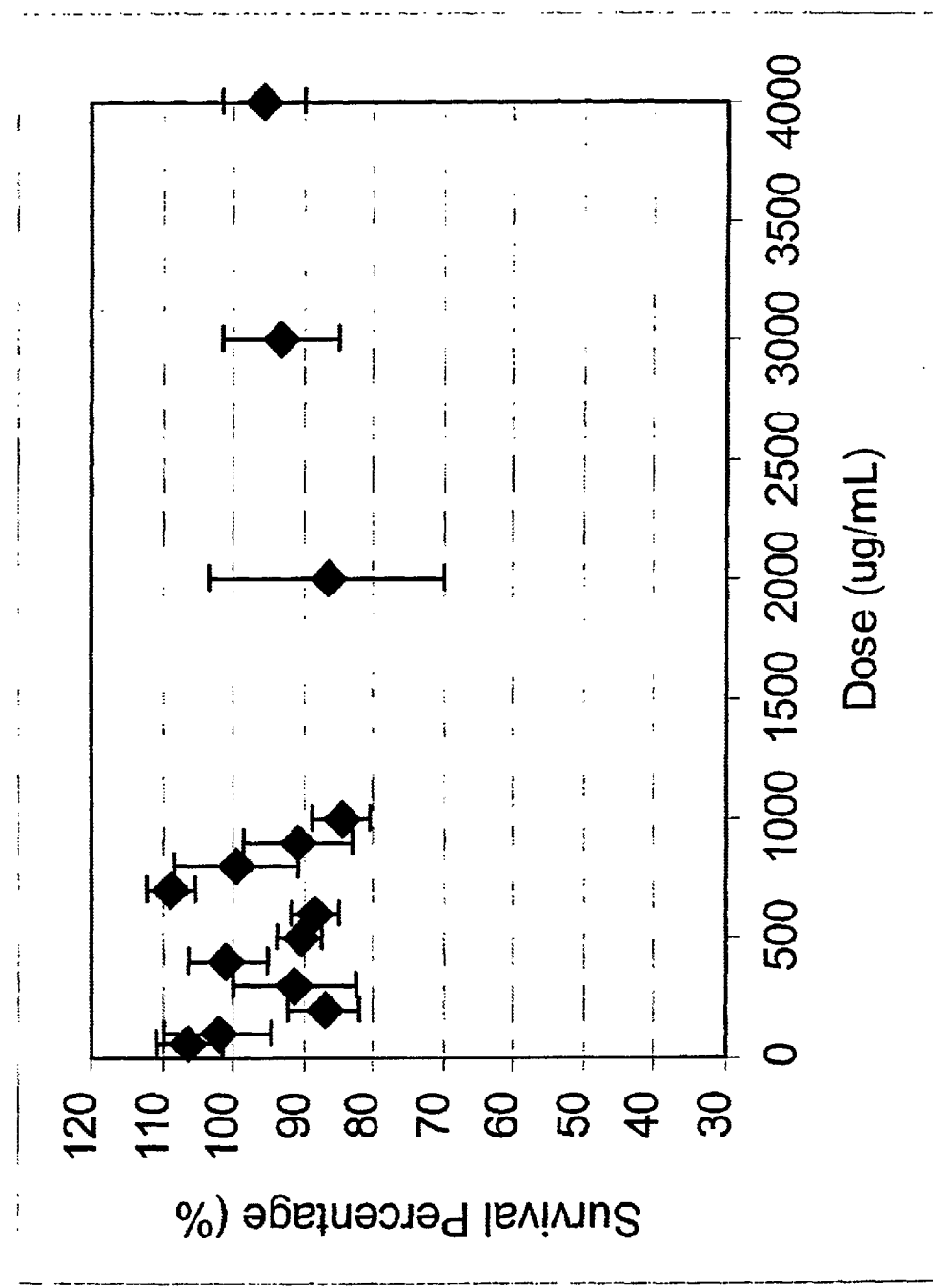
FIG. 15 is a scatter plot of the cytotoxicity of poly(lactide-co-ethylene-ethylphosphate), PLE90, microspheres on HeLa cells.

A standard oil-in-water emulsion solvent evaporation method was used for preparation of the microspheres. Cytotoxicity of PLE90 was evaluated using the WST-1 dye reduction assay. HeLa cells were seeded in a 96 well plate 24 hours before the assay at the density of 2–5×10$^4$ cells/well. The cells were incubated for 4 hours with 100 µL of DMEM medium complemented with 10% fetal bovine serum (FBS) containing different concentrations of PLE90 microspheres. The medium in each well was replaced with 100 µL fresh complete medium and cells were cultured for an additional 20 hrs. Ten microliters of WST-1 reagent was added to each well and allowed to react for 4 hours at 37° C. The absorbance of the supernatant at 450 nm (use 655 nm as a reference wavelength) was measured using a microplate reader. Cell proliferation assay indicated that PLE90 exhibited non-toxicity within the experimental concentration. FIG. 15 is a scatter plot of the cytotoxicity of PLE 90 microspheres on HeLa cells.

EXAMPLE 6
Solubility of Poly(lactide-co-ethylene Ethylphosphate) Conditions Including Concentration and Temperature for Determining Tabulated Data

TABLE 4

Solubility of poly($\epsilon$-caprolactone-co-ethylene ethylphosphate), PCE85 (85 mole % caprolactone repeat units), and poly(lactide-co-ethylene ethylphosphate), PLE (90 mole % lactide)

|  | PCL | PCE85 |
| --- | --- | --- |
| Dichloromethane | + | + |
| Chloroform | + | + |
| Benzene | + |  |
| Acetone | − | + |
| Ethyl acetate | − | + |
| Tetrahydrofuran | + | + |
| Methanol | − | − |
| Diethyl Ether | − | − |

EXAMPLE 7
Degradation of Poly(lactide-co-ethylene-ethylphosphate) with 90 Mole % Lactide Monomer Units (PLE 90) in pH 7.4 PBS at 37° C.

The in vitro degradation study was conducted by placing disc samples in 5 ml 0.1 M pH 7.4 PBS at 37° C. Discs of 8 mm in diameter and 0.3 mm thick were compression molded at room temperature and 150 MPa, yielding samples about 15 mg in weight. The samples were removed at different time points, washed 3 times with distilled water and dried to constant weight under vacuum.

Figure 16:
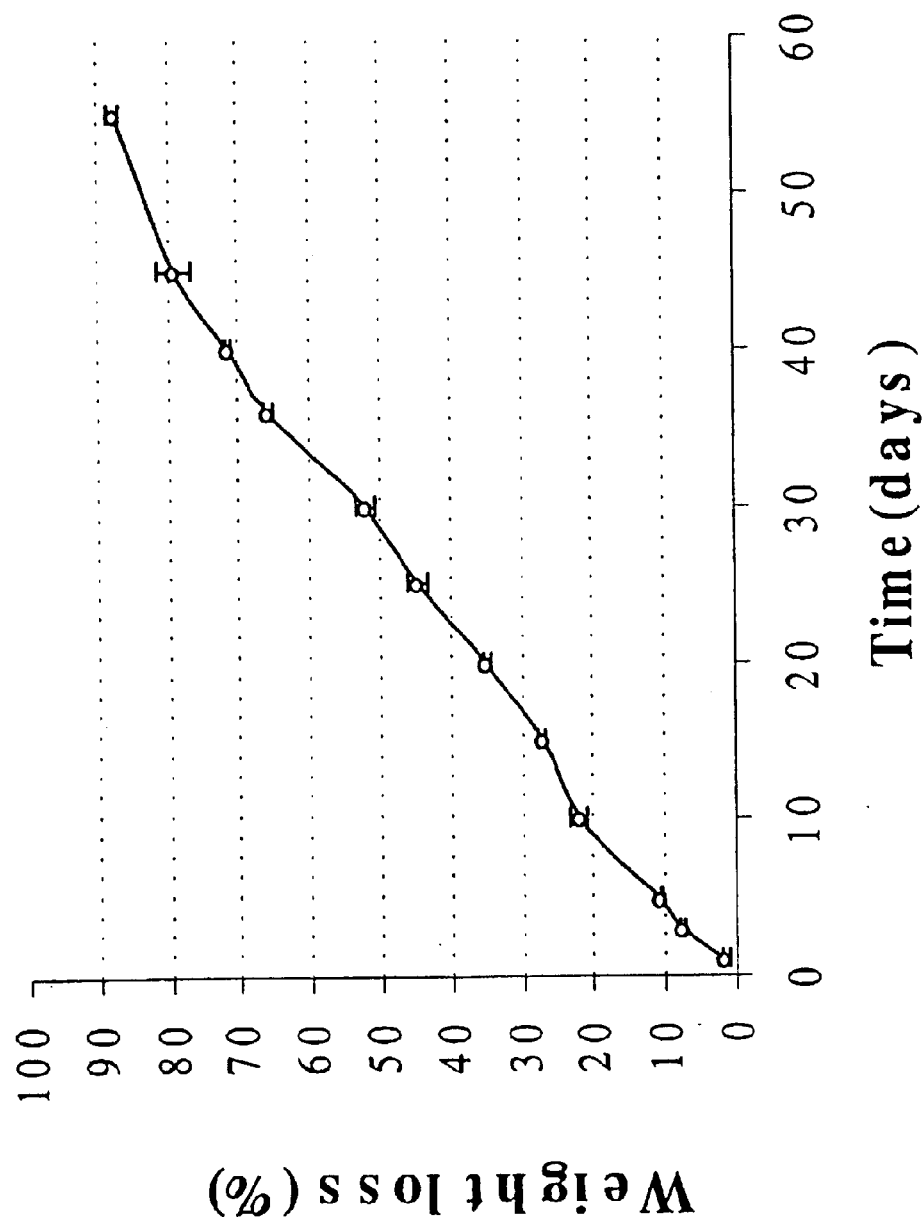
FIG. 16 is a plot of polymer degradation of poly(lactide-co-ethylene-ethylphosphate) at pH 7.4 prenatal bovine serum at 37° C.

Introduction of the phosphate units in the backbone accelerated the degradation rate and eliminated the typical biphasic degradation behavior of PLA. When incubated in pH 7.4 phosphate buffer at 37° C., PLE 90 (D,L-LA/EEP= 90:10, molar ratio) showed a steady degradation rate, with a 50% mass loss in 30 days (FIG. 16). Even compared to low molecular PLA, this is a significantly higher degradation rate. Of interest in the near linear degradation profile up to 90% mass loss. Other PLA copolymers, such as PLA/PEO/ PLA, also degrades at a steady rate. Compared to these block copolymers, the PLE would be expected to be even more labile because of the cleavable phosphate bond.

The following references are incorporated herein by reference.

Jie Wen, Ren-Xi Zhuo (1998), Preparation and characterization of poly(D,L-lactide-co-ethylene methyl phosphate), Polymer International, 47(4), 503–509.

Ren-Xi Zhuo, Jie Wen and Lu Wang (1999), Polymerization of ethylene methyl phosphate in the presence of sodium poly(ethylene glycol)ate, Chinese Journal of Polymer Science, 17: (3) 259–264 1999.

Although a preferred embodiment of the invention has been described using specific terms, such description is for illustrative purposes only, and it is to be understood that changes and variations may be made without departing from the spirit or scope of the following claims.

What is claimed is:

1. A biodegradable polymer comprising at least one repeat unit according to formula A:

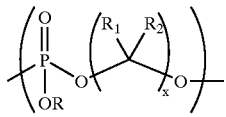

wherein
R is hydrogen, optionally substituted alkyl, optionally substituted heteroalkyl, optionally substituted alkenyl, optionally substituted alkynyl, or optionally substituted cycloalkyl;

$R^1$ and $R^2$ are each independently chosen from the group consisting of H, optionally substituted alkyl, optionally substituted heteroalkyl, optionally substituted alkenyl, optionally substituted alkynyl, and optionally substituted;

x is 2, 3, or 4; and at least one repeat unit selected from the group consisting of optionally substituted alkyl, optionally substituted heteroalkyl, optionally substituted alkenyl, optionally substituted alkynyl, —O(CR$_1$R$_2$)$_c$C(O)— where c is between about 1 and about 10, (CH$_2$)$_a$—{O(CH$_2$)$_a$}$_b$— where a is between about 1 and about 7 and b is between about 1 and about 500, optionally substituted aryl, and optionally substituted heteroaryl; or at least one repeat unit according to formula B:

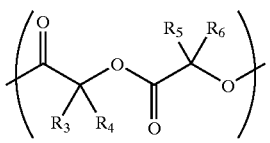

wherein
$R^3$, $R^4$, $R^5$ and $R^6$ are each independently chosen from the group consisting of H, optionally substituted heteroalkyl, optionally substituted alkyl, optionally substituted C$_{2-12}$-alkenyl, optionally substituted C$_{2-12}$-alkynyl, and optionally substituted alkoxy.

2. A polymer of claim 1, wherein the polymer comprises polymer chains that are not crosslinked.

3. A polymer of claim 1, the polymer comprising repeat units as in formula I:

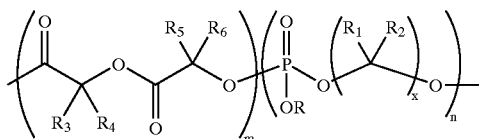

wherein
R is hydrogen, optionally substituted alkyl, optionally substituted C$_{2-12}$-alkenyl, optionally substituted heteroalkyl, optionally substituted C$_{2-12}$-alkynyl, or optionally substituted C$_{5-8}$-cycloalkyl;

$R^1$ and $R^2$ are each independently chosen from the group consisting of H, optionally substituted alkyl, optionally substituted C$_{2-12}$-alkenyl, optionally substituted heteroalkyl, optionally substituted C$_{2-12}$-alkynyl, and optionally substituted alkoxy;

x is 2, 3, or 4;

n and m are non-negative integers;

n+m is about 5 to about 2000; and m:n is between about 1:100 to about 100:1.

4. The polymer of claim 3, wherein
x is 2;
R is C$_{1-6}$-alkyl;
$R^1$ and $R^2$ are independently selected at each occurrence from the group consisting of hydrogen, methyl and ethyl;
$R^3$ and $R^5$ are hydrogen;
$R^4$ is hydrogen or C$_{1-6}$-alkyl; and,
$R^6$ is C$_{1-6}$-alkyl.

5. A polymer of claim 1, the polymer comprising recurring monomeric repeat units in formula II:

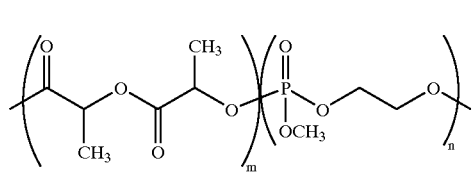

wherein
n and m are non-negative integers;
n+m is about 5 to about 2000; and
m:n is between about 1:100 to about 100:1.

6. A polymer of claim 1, the polymer comprising recurring monomeric repeat units in formula IIA:

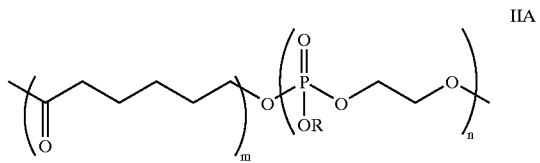

wherein
R is methyl or ethyl;
n and m are non-negative integers;
n+m is about 5 to about 2000; and
m:n is between about 1:100 to about 100:1.

7. A polymer of claim 4, the polymer comprising repeat units as in formula III:

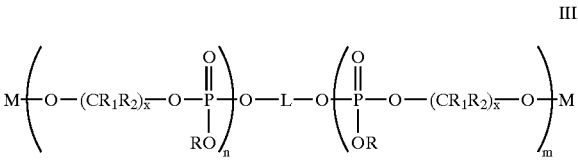

wherein
L is optionally substituted alkyl, optionally substituted heteroalkyl, optionally substituted C$_{2-20}$-alkenyl, optionally substituted C$_{2-20}$-alkynyl, —(CH$_2$)$_a$—{O (CH$_2$)$_a$}$_b$, where a is between about 1 and about 7 and b is between about 1 and about 500, optionally substituted aryl, or optionally substituted heteroaryl;

x is 2, 3, or 4;

R is hydrogen, optionally substituted alkyl, optionally substituted heteroalkyl, optionally substituted $C_{2-12}$-alkenyl, optionally substituted $C_{2-12}$-alkynyl, or optionally substituted $C_{5-8}$-cycloalkyl;

$R^1$ and $R^2$ are each independently chosen from the group consisting of H, optionally substituted alkyl, optionally substituted heteroalkyl, optionally substituted $C_{2-12}$-alkenyl, optionally substituted $C_{2-12}$-alkynyl, and optionally substituted alkoxy;

M is H, Li, Na, or K;

n and m are non-negative integers;

n+m is about 5 to about 2000; and m:n is between about 1:100 to about 100:1.

8. A polymer of claim 1, the polymer comprising repeat units as in formula IV:

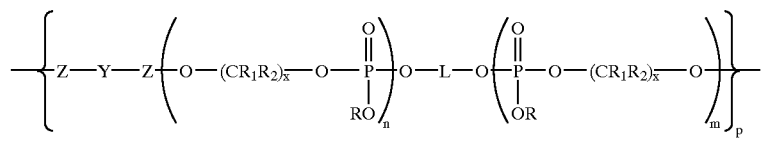

wherein

L is optionally substituted alkyl, optionally substituted $C_{2-20}$-alkenyl, optionally substituted $C_{2-20}$-alkynyl, optionally substituted heteroalkyl, —$(CH_2)_a$—{O$(CH_2)_a$}$_b$ where a is between about 1 and about 7 and b is between about 1 and about 500, optionally substituted aryl, or optionally substituted heteroaryl;

x is 2, 3, or 4;

R is hydrogen, optionally substituted alkyl, optionally substituted $C_{2-12}$-alkenyl, optionally substituted $C_{2-12}$-alkynyl, optionally substituted heteroalkyl, or optionally substituted $C_{5-8}$-cycloalkyl;

$R^1$ and $R^2$ are each independently chosen from the group consisting of H, optionally substituted alkyl, optionally substituted heteroalkyl, optionally substituted $C_{2-12}$-alkenyl, optionally substituted $C_{2-12}$-alkynyl, and optionally substituted alkoxy;

n and m are non-negative integers;

n+m is about 5 to about 2000;

m:n is between about 1:100 to about 100:1;

p is between about 2 and about 500;

Z is chosen from the group consisting of —C(O)—, —C(O)NH—, —C(OH)HCH$_2$—, and —C(CH$_2$OH)H—; and Y is optionally substituted alkyl, optionally substituted heteroalkyl, optionally substituted $C_{2-20}$-alkenyl, optionally substituted $C_{2-20}$-alkynyl, optionally substituted $C_{5-8}$cycloalkyl, —$(CH_2)_a$—{O$(CH_2)_a$}$_b$ where a is between about 1 and about 7 and b is between about 1 and about 100, optionally substituted aryl or optionally substituted heteroaryl.

9. The polymer of claim 8, wherein:

x is 2;

L is —$(CH_2)_a$—{O$(CH_2)_a$}$_b$ where a is between about 1 and about 7 and b is between about 1 and about 500;

Y is alkyl or aryl;

Z is —C(O)— or —C(O)NH—;

R is methyl or ethyl; and, $R^1$ and $R^2$ are hydrogen.

10. A polymer of claim 1, the polymer comprising repeat units as in formula V:

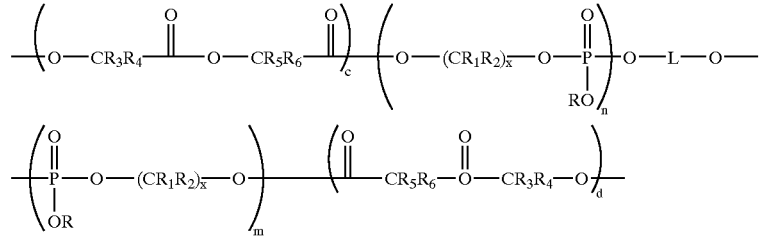

wherein

L is optionally substituted alkyl, optionally substituted $C_{2-20}$-alkenyl, optionally substituted $C_{2-20}$-alkynyl, optionally substituted heteroalkyl, —$(CH_2)_a$—{O$(CH_2)_a$}$_b$ where a is between about 1 and about 7 and b is between about 1 and about 500, optionally substituted aryl, or optionally substituted heteroaryl;

x is 2, 3, or 4;

R is hydrogen, optionally substituted alkyl, optionally substituted $C_{2-12}$-alkenyl, optionally substituted $C_{2-12}$-alkynyl, optionally substituted heteroalkyl, or optionally substituted $C_{5-8}$-cycloalkyl;

$R^1$ and $R^2$ are each independently chosen from the group consisting of H, optionally substituted alkyl, optionally substituted heteroalkyl, optionally substituted $C_{2-12}$-alkenyl, optionally substituted $C_{2-12}$-alkynyl, and optionally substituted alkoxy;

n and m are non-negative integers;

n+m is about 5 to about 2000;

m:n is between about 1:100 to about 100:1;

c and d are non-negative integers;

c+d is about 5 to about 2000; and (m+n):(c+d) is between about 1:100 and 100:1.

11. A process for preparing a biodegradable polymer comprising the recurring monomeric units of formula I:

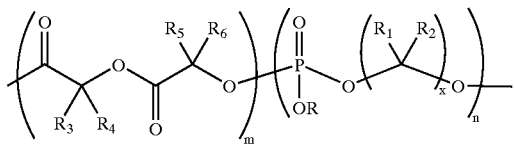

I wherein:
- R is hydrogen, optionally substituted $C_{2-12}$-alkenyl, optionally substituted heteroalkyl, optionally substituted $C_{2-12}$-alkynyl, or optionally substituted alkyl;
- $R^1$, $R^2$, $R^3$, $R^4$, $R^5$ and $R^6$ are each independently chosen from the group consisting of hydrogen, optionally substituted alkyl, optionally substituted heteroalkyl, optionally substituted $C_{2-12}$-alkenyl, optionally substituted $C_{2-12}$-alkynyl, and optionally substituted alkoxy;
- x is 2, 3, or 4;
- n and m are non-negative integers;
- n+m is about 5 to about 2000; and,
- m:n is between about 1:100 to about 100:1;

wherein the process comprising the steps of:
- contacting at least one glycolide derivative and at least one cyclic phosphate; and
- polymerizing the glycolide derivative and the cyclic phosphate under conditions conducive to preparing the biodegradable polymer.

12. The process of claim 11, wherein the glycolide derivative is a compound according to formula VI:

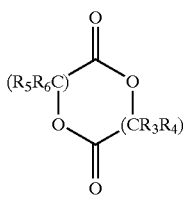

VI wherein:
- $R^4$ and $R^6$ are independently selected from the group consisting of hydrogen, alkyl, $C_{2-12}$-alkenyl, $C_{2-12}$-alkynyl, and alkoxy such that both $R^4$ and $R^6$ are not hydrogen; and
- $R^3$ and $R^5$ are hydrogen.

13. The process of claim 11, wherein the cyclic phosphate is a compound according to formula VII:

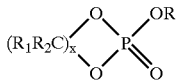

VII wherein
R, independently selected at each occurrence from the group consisting of, optionally substituted alkyl, optionally substituted $C_{2-12}$-alkenyl, optionally substituted heteroalkyl, optionally substituted $C_{2-12}$-alkynyl, and optionally substituted alkoxy;

$R^1$ and $R^2$ are independently selected at each occurrence from the group consisting of hydrogen, optionally substituted alkyl, optionally substituted heteroalkyl, optionally substituted $C_{2-12}$-alkenyl, optionally substituted $C_{2-12}$-alkynyl, and optionally substituted alkoxy; and x is 2, 3 or 4.

14. A process for preparing a biodegradable polymer comprising the recurring monomeric units of formula III:

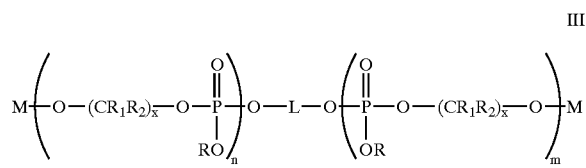

III wherein:

R is hydrogen, optionally substituted $C_{2-12}$-alkenyl, optionally substituted heteroalkyl, optionally substituted $C_{2-12}$-alkynyl, or optionally substituted alkyl;

$R^1$ and $R^2$ are each independently chosen at each occurrence from the group consisting of hydrogen, optionally substituted alkyl, optionally substituted heteroalkyl, optionally substituted $C_{2-12}$-alkenyl, optionally substituted $C_{2-12}$-alkynyl, and optionally substituted alkoxy;

L is chosen from the group consisting of optionally substituted $C_{2-12}$-alkyl, optionally substituted heteroalkyl, optionally substituted $C_{2-20}$-alkenyl, optionally substituted $C_{2-20}$-alkynyl, or —$(CH_2)_a$—$\{O$—$(CH_2)_a\}_b$—, wherein each a is 1–6 and b is 1–500;

n and m are non-negative integers;

n+m is about 5 to about 2000;

x is 2, 3 or 4; and

M is independently chosen at each occurrence of M from the group consisting of H, Na, Li, and K;

the process comprising the steps of:

contacting at least one cyclic phosphate with an initiator compound, HO—L—OH;

polymerizing the cyclic phosphate with the initiator compound under conditions conducive to preparing the biodegradable polymer.

15. A process for preparing a biodegradable polymer comprising the recurring monomeric units of formula IV:

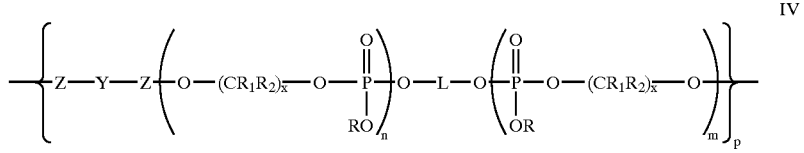

IV wherein
L is optionally substituted alkyl, optionally substituted $C_{2-20}$-alkenyl, optionally substituted $C_{2-20}$-alkynyl, —$(CH_2)_a$—$\{O(CH_2)_a\}_b$ where a is between about 1 and about 7 and b is between about 1 and about 500, aryl, or heteroaryl;

x is 2, 3, or 4;

p is between about 2 and about 500;

R is hydrogen, optionally substituted alkyl, optionally substituted heteroalkyl, optionally substituted $C_{2-12}$-alkenyl, optionally substituted $C_{2-12}$-alkynyl, or $C_{5-8}$-cycloalkyl;

$R^1$ and $R^2$ are each independently chosen from the group consisting of hydrogen, optionally substituted alkyl, optionally substituted $C_{2-12}$-alkenyl, optionally substituted heteroalkyl, optionally substituted $C_{2-12}$-alkynyl, and optionally substituted alkoxy;

n and m are non-negative integers;

n+m is about 5 to about 2000;

m:n is between about 1:100 to about 100:1;

Z is chosen from the group consisting of —C(O)—, —C(O)NH—, —C(OH)HCH$_2$—, and —C(CH$_2$OH)H—;

Y is alkyl, $C_{2-20}$-alkenyl, optionally substituted heteroalkyl, $C_{2-20}$-alkynyl, $C_{5-8}$cycloalkyl, —$(CH_2)_a$—$\{O(CH_2)_a\}_b$ where a is between about 1 and about 7 and b is between about 1 and about 100, aryl or heteroaryl; and, the process comprising the steps of:

making the biodegradable polymer of claim 13;

contacting the biodegradable polymer of claim 13 with a compound with two functional groups capable of reacting with an alcohol to form a covalent bond; and polymerizing the biodegradable polymer and the compound with two functional groups capable of reacting with an alcohol under conditions conducive to preparing the biodegradable polymer according to formula IV.

16. A process for preparing a biodegradable polymer comprising the recurring monomeric units of formula V:

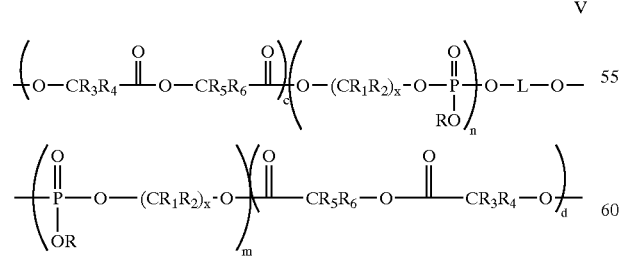

V wherein
L is optionally substituted alkyl, optionally substituted $C_{2-20}$-alkenyl, optionally substituted $C_{2-20}$-alkynyl, —$(CH_2)_a$—$\{O(CH_2)_a\}_b$ where a is between about 1 and about 7 and b is between about 1 and about 500, optionally substituted aryl, or optionally substituted heteroaryl;

x is 2, 3, or 4;

R is hydrogen, optionally substituted alkyl, optionally substituted $C_{2-12}$-alkenyl, optionally substituted heteroalkyl, optionally substituted $C_{2-12}$-alkynyl, or $C_{5-8}$-cycloalkyl;

$R^1$ and $R^2$ are each independently chosen from the group consisting of hydrogen, optionally substituted alkyl, optionally substituted $C_{2-12}$-alkenyl, optionally substituted $C_{2-12}$-alkynyl, optionally substituted heteroalkyl, and optionally substituted alkoxy;

n and m are non-negative integers;

n+m is about 5 to about 2000;

m:n is between about 1:100 to about 100:1;

c and d are non-negative integers;

c+d is about 5 to about 2000;

(m+n):(c+d) is between about 1:100 and 100:1; and, the process comprising the steps of:

making at least one biodegradable polymer of claim 13;

contacting the biodegradable polymer of claim 13 with at least one glycolide derivative; and polymerizing the glycolide derivative under conditions conducive to the preparing a biodegradable polymer according to formula V.

17. A biodegradable polymer composition comprising:

(a) at least one biologically active substance; and (b) a biodegradable polymer comprising at least one repeat unit according to formula A:

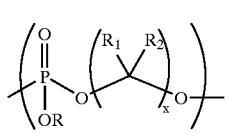

A wherein
R is hydrogen, optionally substituted alkyl, optionally substituted $C_{2-12}$-alkenyl, optionally substituted heteroalkyl, optionally substituted $C_{2-12}$-alkynyl, or optionally substituted $C_{5-8}$-cycloalkyl;

$R^1$ and $R^2$ are each independently chosen from the group consisting of H, optionally substituted alkyl, optionally substituted heteroalkyl, optionally substituted $C_{2-12}$-alkenyl, optionally substituted $C_{2-12}$-alkynyl, and optionally substituted alkoxy;

x is 2, 3, or 4; and at least one repeat unit selected from the group consisting of alkyl, $C_{2-20}$-alkenyl, $C_{2-20}$-alkynyl, optionally substituted heteroalkyl, —O(CR$_1$R$_2$)$_c$C(O)— where c is between about 1 and about 10, —$(CH_2)_a$—$\{O(CH_2)_a\}_b$— where a is between about 1 and about 7 and b is between about 1 and about 500, aryl, and heteroaryl; or at least one repeat unit according to formula B:

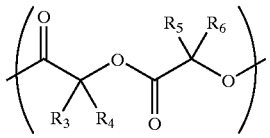

wherein $R^3$, $R^4$, $R^5$ and $R^6$ are each independently chosen from the group consisting of H, optionally substituted alkyl, optionally substituted $C_{2-12}$-alkenyl, optionally substituted $C_{2-12}$-alkynyl, optionally substituted heteroalkyl, and optionally substituted alkoxy.

18. The polymer composition of claim 17, wherein the polymer comprising repeat units as in formula I:

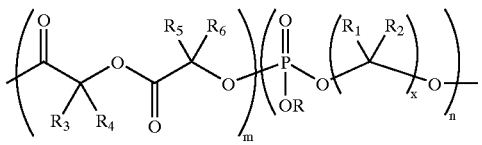

wherein

R is hydrogen, optionally substituted alkyl, optionally substituted $C_{2-12}$-alkenyl, optionally substituted $C_{2-12}$-alkynyl, optionally substituted heteroalkyl, or optionally substituted $C_{5-8}$-cycloalkyl;

$R^1$, $R^2$, $R^3$, $R^4$, $R^5$ and $R^6$ are each independently chosen from the group consisting of H, optionally substituted alkyl, optionally substituted heteroalkyl, optionally substituted $C_{2-12}$-alkenyl, optionally substituted $C_{2-12}$-alkynyl, and optionally substituted alkoxy;

x is 2, 3, or 4;

n and m are non-negative integers;

n+m is about 5 to about 2000; and m:n is between about 1:100 to about 100:1.

19. The polymer composition of claim 18, wherein x is 2;

R is methyl or ethyl;

$R^4$ and $R^6$ are methyl; and, $R^1$, $R^2$, $R^3$ and $R^5$ are hydrogen.

20. The polymer composition of claim 17, wherein the polymer comprising repeat units as in formula III:

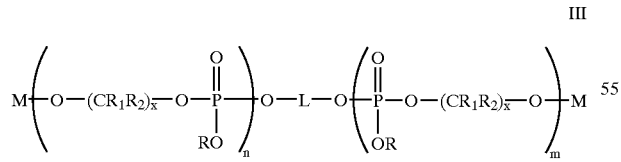

wherein

L is optionally substituted alkyl, optionally substituted $C_{2-20}$-alkenyl, optionally substituted $C_{2-20}$-alkynyl, optionally substituted heteroalkyl, $-(CH_2)_a-\{O(CH_2)_a\}_b$ where a is between about 1 and about 7 and b is between about 1 and about 500, optionally substituted aryl, or optionally substituted heteroaryl;

x is 2, 3, or 4;

R is hydrogen, optionally substituted alkyl, optionally substituted $C_{2-12}$-alkenyl, optionally substituted $C_{2-12}$-alkynyl, optionally substituted heteroalkyl, or optionally substituted $C_{5-8}$-cycloalkyl;

$R^1$ and $R^2$ are each independently chosen from the group consisting of hydrogen, optionally substituted alkyl, optionally substituted heteroalkyl, optionally substituted $C_{2-12}$-alkenyl, optionally substituted $C_{2-12}$-alkynyl, and optionally substituted alkoxy;

M is H, Li, Na, or K;

n and m are non-negative integers;

n+m is about 5 to about 2000; and m:n is between about 1:100 to about 100:1.

21. The polymer composition of claim 17, wherein the polymer comprising repeat units as in formula IV:

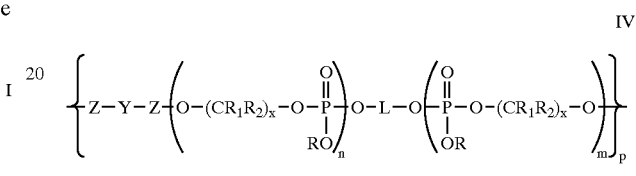

wherein

L is optionally substituted alkyl, optionally substituted $C_{2-20}$-alkenyl, optionally substituted $C_{2-20}$-alkynyl, $-(CH_2)_a-\{O(CH_2)_a\}_b$ where a is between about 1 and about 7 and b is between about 1 and about 500, optionally substituted aryl, or optionally substituted heteroaryl;

x is 2, 3, or 4;

p is between about 2 and about 500;

R is hydrogen, optionally substituted alkyl, optionally substituted $C_{2-12}$-alkenyl, optionally substituted $C_{2-12}$-alkynyl, optionally substituted heteroalkyl, or optionally substituted $C_{5-8}$-cycloalkyl;

$R^1$ and $R^2$ are each independently chosen from the group consisting of hydrogen, optionally substituted alkyl, optionally substituted heteroalkyl, optionally substituted $C_{2-12}$-alkenyl, optionally substituted $C_{2-12}$-alkynyl, and optionally substituted alkoxy;

n and m are non-negative integers;

n+m is about 5 to about 2000;

m:n is between about 1:100 to about 100:1;

Z is chosen from the group consisting of $-C(O)-$, $-C(O)NH-$, $-C(OH)HCH_2-$, and $-C(CH_2OH)H-$; and, Y is optionally substituted alkyl, optionally substituted heteroalkyl, optionally substituted $C_{2-20}$-alkenyl, optionally substituted $C_{2-20}$-alkynyl, optionally substituted $C_{5-8}$cycloalkyl, $-(CH_2)_a-\{O(CH_2)_a\}_b$ where a is between about 1 and about 7 and b is between about 1 and about 100, optionally substituted aryl or optionally substituted heteroaryl.

22. The polymer composition of claim 17, wherein the polymer comprising repeat units as in formula V:

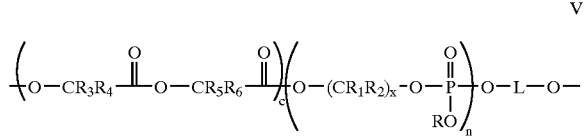

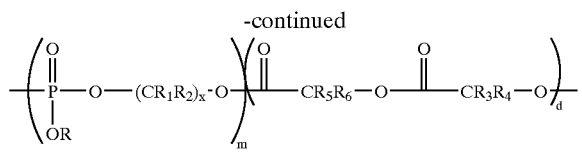

wherein
- L is optionally substituted alkyl, optionally substituted $C_{2-20}$-alkenyl, optionally substituted $C_{2-20}$-alkynyl, optionally substituted heteroalkyl, $-(CH_2)_a-\{O(CH_2)_a\}_b$, where a is between about 1 and about 7 and b is between about 1 and about 500, optionally substituted aryl, or optionally substituted heteroaryl;
- x is 2, 3, or 4;
- R is hydrogen, optionally substituted alkyl, optionally substituted heteroalkyl, optionally substituted $C_{2-12}$-alkenyl, optionally substituted $C_{2-12}$-alkynyl, or optionally substituted $C_{5-8}$-cycloalkyl;
- $R^1$ and $R^2$ are each independently chosen from the group consisting of hydrogen, optionally substituted alkyl, optionally substituted $C_{2-12}$-alkenyl, optionally substituted heteroalkyl, optionally substituted $C_{2-12}$-alkynyl, and optionally substituted alkoxy;
- n and m are non-negative integers;
- n+m is about 5 to about 2000;
- m:n is between about 1:100 to about 100:1;
- c and d are non-negative integers;
- c+d is about 5 to about 2000; and,
- (m+n):(c+d) is between about 1:100 and 100:1.

23. The polymer composition of claim 17, wherein the polymer is soluble in at least one of the solvents selected from the group consisting of acetone, dimethylene chloride, chloroform, ethyl acetate, DMAC, N-methylpyrrolidone, dimethylformamide and dimehtylsulfoxide.

24. The polymer composition of claim 17, wherein the biologically active substance is a therapeutic drug or pro-drug.

25. The polymer composition of claim 24, wherein the biologically active substance is selected from the group consisting of polysaccharides, growth factors, hormones, anti-angiogenesis factors, interferons or cytokines, and pro-drugs of these substances.

26. The polymer composition of claim 24, wherein the drug is selected from the group consisting of anti-neoplastic neoplastic agents, antibiotics, anti-virals, anti-fungals, anti-inflammatories and anticoagulants.

27. The polymer composition of claim 24, wherein the biologically active substance and the polymer form a homogeneous matrix.

* * * * *